(12) United States Patent
Howell et al.

(10) Patent No.: US 12,161,820 B2
(45) Date of Patent: Dec. 10, 2024

(54) RAPIDLY INSERTABLE CENTRAL CATHETERS INCLUDING CATHETER ASSEMBLIES AND METHODS THEREOF

(71) Applicant: Bard Access Systems, Inc., Salt Lake City, UT (US)

(72) Inventors: Glade H. Howell, Draper, UT (US); Jason R. Stats, Layton, UT (US)

(73) Assignee: Bard Access Systems, Inc., Salt Lake City, UT (US)

(*) Notice: Subject to any disclaimer, the term of this patent is extended or adjusted under 35 U.S.C. 154(b) by 365 days.

(21) Appl. No.: 17/358,504

(22) Filed: Jun. 25, 2021

(65) Prior Publication Data

US 2021/0402153 A1    Dec. 30, 2021

Related U.S. Application Data

(60) Provisional application No. 63/045,649, filed on Jun. 29, 2020.

(51) Int. Cl.
*A61M 25/06* (2006.01)
*A61M 5/31* (2006.01)
(Continued)

(52) U.S. Cl.
CPC .......... *A61M 25/0606* (2013.01); *A61M 5/31* (2013.01); *A61M 25/0026* (2013.01);
(Continued)

(58) Field of Classification Search
CPC ............... A61M 25/0606; A61M 5/31; A61M 25/0026; A61M 25/0054; A61M 25/0097;
(Continued)

(56) References Cited

U.S. PATENT DOCUMENTS 1,013,691 A    1/1912    Shields
3,225,762 A    12/1965   Guttman
(Continued)

FOREIGN PATENT DOCUMENTS

DE    202012006191 U1    7/2012
EP         0653220 A1    5/1995
(Continued)

OTHER PUBLICATIONS

PCT/US2021/057135 filed Oct. 28, 2021 International Preliminary Report on Patentability dated May 2, 2023.
(Continued)

*Primary Examiner* — Brandy S Lee
*Assistant Examiner* — Fatimata Sahra Diop
(74) *Attorney, Agent, or Firm* — Rutan & Tucker LLP

(57) ABSTRACT

Rapidly insertable central catheters ("RICCs") including catheter assemblies and methods thereof are disclosed. A RICC assembly can include a RICC, an introducer, and a coupling system configured to couple the RICC and the introducer together. A catheter tube of the RICC includes a side aperture in a distal-end portion of the catheter tube, which opens into an introducing lumen extending to a distal end of the RICC. The introducer includes an introducer needle extending through the distal end of the RICC when the RICC assembly is in at least a ready-to-deploy state thereof. The introducer is configured to be actuated with a single finger of a hand while holding a distal-end portion of the introducer between a thumb and another finger or fingers of the hand. The coupling system includes a distal coupler slidably attached to the catheter tube proximal of the side aperture.

21 Claims, 5 Drawing Sheets

(51) Int. Cl.
*A61M 25/00* (2006.01)
*A61M 25/09* (2006.01)

(52) U.S. Cl.
CPC .... *A61M 25/0054* (2013.01); *A61M 25/0097* (2013.01); *A61M 25/0668* (2013.01); *A61M 25/09* (2013.01); *A61M 2202/0413* (2013.01); *A61M 2205/586* (2013.01); *A61M 2210/125* (2013.01)

(58) Field of Classification Search
CPC .............. A61M 25/0668; A61M 25/09; A61M 2202/0413; A61M 2205/586; A61M 2210/125; A61M 5/3129; A61M 5/31513; A61M 5/3137; A61M 5/31505; A61M 5/3293; A61M 25/0111; A61M 25/0693; A61M 25/09041; A61M 25/007; A61M 25/008; A61M 25/0084; A61M 25/0102; A61M 25/0113; A61M 25/065; A61M 2210/12; A61M 25/0043; A61B 5/15003; A61B 5/153
See application file for complete search history.

(56) References Cited

U.S. PATENT DOCUMENTS

| | | |
|---|---|---|
| 3,382,872 A | 5/1968 | Rubin |
| 3,570,485 A | 3/1971 | Reilly |
| 3,890,976 A | 6/1975 | Bazell et al. |
| 4,205,675 A | 6/1980 | Vaillancourt |
| 4,292,970 A | 10/1981 | Hession, Jr. |
| 4,468,224 A | 8/1984 | Enzmann et al. |
| 4,525,157 A | 6/1985 | Vaillancourt |
| 4,581,019 A | 4/1986 | Curelaru et al. |
| 4,594,073 A | 6/1986 | Stine |
| 4,702,735 A | 10/1987 | Luther et al. |
| 4,743,265 A | 5/1988 | Whitehouse et al. |
| 4,766,908 A | 8/1988 | Clement |
| 4,863,432 A | 9/1989 | Kvalo |
| 4,950,252 A | 8/1990 | Luther et al. |
| 4,994,040 A | 2/1991 | Cameron et al. |
| 5,017,259 A | 5/1991 | Kohsai |
| 5,040,548 A | 8/1991 | Yock |
| 5,057,073 A | 10/1991 | Martin |
| 5,112,312 A | 5/1992 | Luther |
| 5,115,816 A | 5/1992 | Lee |
| 5,120,317 A | 6/1992 | Luther |
| 5,158,544 A | 10/1992 | Weinstein |
| 5,188,593 A | 2/1993 | Martin |
| 5,195,962 A | 3/1993 | Martin et al. |
| 5,207,650 A | 5/1993 | Martin |
| RE34,416 E | 10/1993 | Lemieux |
| 5,267,958 A | 12/1993 | Buchbinder et al. |
| 5,295,970 A | 3/1994 | Clinton et al. |
| 5,306,247 A | 4/1994 | Pfenninger |
| 5,312,361 A | 5/1994 | Zadini et al. |
| 5,322,512 A | 6/1994 | Mohiuddin |
| 5,328,472 A | 7/1994 | Steinke et al. |
| 5,350,358 A | 9/1994 | Martin |
| 5,358,495 A | 10/1994 | Lynn |
| 5,368,567 A | 11/1994 | Lee |
| 5,378,230 A | 1/1995 | Mahurkar |
| 5,380,290 A | 1/1995 | Makower et al. |
| 5,389,087 A | 2/1995 | Miraki |
| 5,439,449 A | 8/1995 | Mapes et al. |
| 5,443,457 A | 8/1995 | Ginn et al. |
| 5,460,185 A | 10/1995 | Johnson et al. |
| 5,489,271 A | 2/1996 | Andersen |
| 5,573,520 A | 11/1996 | Schwartz et al. |
| 5,683,370 A | 11/1997 | Luther et al. |
| 5,713,876 A | 2/1998 | Bogert et al. |
| 5,718,678 A | 2/1998 | Fleming, III |
| 5,772,636 A | 6/1998 | Brimhall et al. |
| 5,885,251 A | 3/1999 | Luther |
| 5,919,164 A | 7/1999 | Andersen |
| 5,921,971 A * | 7/1999 | Agro ................ A61M 25/0029 604/523 |
| 5,947,940 A | 9/1999 | Beisel |
| 5,957,893 A | 9/1999 | Luther et al. |
| 5,971,957 A | 10/1999 | Luther et al. |
| 6,159,198 A | 12/2000 | Gardeski et al. |
| 6,206,849 B1 | 3/2001 | Martin et al. |
| 6,228,062 B1 | 5/2001 | Howell et al. |
| 6,475,187 B1 | 11/2002 | Gerberding |
| 6,551,284 B1 | 4/2003 | Greenberg et al. |
| 6,606,515 B1 | 8/2003 | Windheuser et al. |
| 6,616,630 B1 | 9/2003 | Woehr et al. |
| 6,626,869 B1 | 9/2003 | Bint |
| 6,638,252 B2 | 10/2003 | Moulton et al. |
| 6,716,228 B2 | 4/2004 | Tal |
| 6,726,659 B1 | 4/2004 | Stocking et al. |
| 6,819,951 B2 | 11/2004 | Patel et al. |
| 6,821,287 B1 | 11/2004 | Jang |
| 6,926,692 B2 | 8/2005 | Katoh et al. |
| 6,962,575 B2 | 11/2005 | Tal |
| 6,991,625 B1 | 1/2006 | Gately et al. |
| 6,994,693 B2 | 2/2006 | Tal |
| 6,999,809 B2 | 2/2006 | Currier et al. |
| 7,025,746 B2 | 4/2006 | Tal |
| 7,029,467 B2 | 4/2006 | Currier et al. |
| 7,037,293 B2 | 5/2006 | Carrillo et al. |
| 7,074,231 B2 | 7/2006 | Jang |
| 7,094,222 B1 | 8/2006 | Siekas et al. |
| 7,141,050 B2 | 11/2006 | Deal et al. |
| 7,144,386 B2 | 12/2006 | Korkor et al. |
| 7,311,697 B2 | 12/2007 | Osborne |
| 7,364,566 B2 | 4/2008 | Elkins et al. |
| 7,377,910 B2 | 5/2008 | Katoh et al. |
| 7,390,323 B2 | 6/2008 | Jang |
| D600,793 S | 9/2009 | Bierman et al. |
| D601,242 S | 9/2009 | Bierman et al. |
| D601,243 S | 9/2009 | Bierman et al. |
| 7,594,911 B2 | 9/2009 | Powers et al. |
| 7,691,093 B2 | 4/2010 | Brimhall |
| 7,722,567 B2 | 5/2010 | Tal |
| D617,893 S | 6/2010 | Bierman et al. |
| D624,643 S | 9/2010 | Bierman et al. |
| 7,819,889 B2 | 10/2010 | Healy et al. |
| 7,857,788 B2 | 12/2010 | Racz |
| D630,729 S | 1/2011 | Bierman et al. |
| 7,909,797 B2 | 3/2011 | Kennedy, II et al. |
| 7,909,811 B2 | 3/2011 | Agro et al. |
| 7,922,696 B2 | 4/2011 | Tal et al. |
| 7,938,820 B2 | 5/2011 | Webster et al. |
| 7,967,834 B2 | 6/2011 | Tal et al. |
| 7,976,511 B2 | 7/2011 | Fojtik |
| 7,985,204 B2 | 7/2011 | Katoh et al. |
| 8,073,517 B1 | 12/2011 | Burchman |
| 8,105,286 B2 | 1/2012 | Anderson et al. |
| 8,192,402 B2 | 6/2012 | Anderson et al. |
| 8,202,251 B2 | 6/2012 | Bierman et al. |
| 8,206,356 B2 | 6/2012 | Katoh et al. |
| 8,361,011 B2 | 1/2013 | Mendels |
| 8,372,107 B2 | 2/2013 | Tupper |
| 8,377,006 B2 | 2/2013 | Tal et al. |
| 8,454,577 B2 | 6/2013 | Joergensen et al. |
| 8,585,858 B2 | 11/2013 | Kronfeld et al. |
| 8,657,790 B2 | 2/2014 | Tal et al. |
| 8,672,888 B2 | 3/2014 | Tal |
| 8,696,645 B2 | 4/2014 | Tal et al. |
| 8,784,362 B2 | 7/2014 | Boutilette et al. |
| 8,827,958 B2 | 9/2014 | Bierman et al. |
| 8,876,704 B2 | 11/2014 | Golden et al. |
| 8,882,713 B1 | 11/2014 | Call et al. |
| 8,900,192 B2 | 12/2014 | Anderson et al. |
| 8,900,207 B2 | 12/2014 | Uretsky |
| 8,915,884 B2 | 12/2014 | Tal et al. |
| 8,956,327 B2 | 2/2015 | Bierman et al. |
| 9,023,093 B2 | 5/2015 | Pal |
| 9,067,023 B2 | 6/2015 | Bertocci |
| 9,126,012 B2 | 9/2015 | McKinnon et al. |
| 9,138,252 B2 | 9/2015 | Bierman et al. |
| 9,180,275 B2 | 11/2015 | Helm |

(56) References Cited

U.S. PATENT DOCUMENTS

| | | |
|---|---|---|
| 9,265,920 B2 | 2/2016 | Rundquist et al. |
| 9,272,121 B2 | 3/2016 | Piccagli |
| 9,445,734 B2 | 9/2016 | Grunwald |
| 9,522,254 B2 | 12/2016 | Belson |
| 9,554,785 B2 | 1/2017 | Walters et al. |
| 9,566,087 B2 | 2/2017 | Bierman et al. |
| 9,675,784 B2 | 6/2017 | Belson |
| 9,713,695 B2 | 7/2017 | Bunch et al. |
| 9,764,117 B2 | 9/2017 | Bierman et al. |
| 9,770,573 B2 | 9/2017 | Golden et al. |
| 9,814,861 B2 | 11/2017 | Boutillette et al. |
| 9,820,845 B2 | 11/2017 | von Lehe et al. |
| 9,861,383 B2 | 1/2018 | Clark |
| 9,872,971 B2 | 1/2018 | Blanchard |
| 9,884,169 B2 | 2/2018 | Bierman et al. |
| 9,889,275 B2 | 2/2018 | Voss et al. |
| 9,913,585 B2 | 3/2018 | McCaffrey et al. |
| 9,913,962 B2 | 3/2018 | Tal et al. |
| 9,981,113 B2 | 5/2018 | Bierman |
| 10,010,312 B2 | 7/2018 | Tegels |
| 10,065,020 B2 | 9/2018 | Gaur |
| 10,086,170 B2 | 10/2018 | Chhikara et al. |
| 10,098,724 B2 | 10/2018 | Adams et al. |
| 10,111,683 B2 | 10/2018 | Tsamir et al. |
| 10,118,020 B2 | 11/2018 | Avneri et al. |
| 10,130,269 B2 | 11/2018 | McCaffrey et al. |
| 10,220,184 B2 | 3/2019 | Clark |
| 10,220,191 B2 | 3/2019 | Belson et al. |
| 10,265,508 B2 | 4/2019 | Baid |
| 10,271,873 B2 | 4/2019 | Steingisser et al. |
| 10,376,675 B2 | 8/2019 | Mitchell et al. |
| 10,675,440 B2 | 6/2020 | Abitabilo et al. |
| 10,806,901 B2 | 10/2020 | Burkholz et al. |
| 10,926,060 B2 | 2/2021 | Stern et al. |
| 11,260,206 B2 * | 3/2022 | Stone .................. A61M 25/065 |
| 11,759,607 B1 | 9/2023 | Biancarelli |
| 2002/0040231 A1 | 4/2002 | Wysoki |
| 2002/0198492 A1 | 12/2002 | Miller et al. |
| 2003/0036712 A1 | 2/2003 | Heh et al. |
| 2003/0060863 A1 | 3/2003 | Dobak |
| 2003/0088212 A1 | 5/2003 | Tal |
| 2003/0100849 A1 | 5/2003 | Jang |
| 2003/0153874 A1 | 8/2003 | Tal |
| 2003/0158514 A1 | 8/2003 | Tal |
| 2004/0015138 A1 | 1/2004 | Currier et al. |
| 2004/0064086 A1 | 4/2004 | Gottlieb et al. |
| 2004/0116864 A1 | 6/2004 | Boudreaux |
| 2004/0116901 A1 | 6/2004 | Appling |
| 2004/0167478 A1 | 8/2004 | Mooney et al. |
| 2004/0193093 A1 | 9/2004 | Desmond |
| 2004/0230178 A1 | 11/2004 | Wu |
| 2005/0004554 A1 | 1/2005 | Osborne |
| 2005/0120523 A1 | 6/2005 | Schweikert |
| 2005/0131343 A1 | 6/2005 | Abrams et al. |
| 2005/0215956 A1 | 9/2005 | Nerney |
| 2005/0245882 A1 | 11/2005 | Elkins et al. |
| 2005/0283221 A1 | 12/2005 | Mann et al. |
| 2006/0009740 A1 | 1/2006 | Higgins et al. |
| 2006/0116629 A1 | 6/2006 | Tal et al. |
| 2006/0129100 A1 | 6/2006 | Tal |
| 2006/0129130 A1 | 6/2006 | Tal et al. |
| 2007/0276288 A1 | 11/2007 | Khaw |
| 2008/0045894 A1 | 2/2008 | Perchik et al. |
| 2008/0125744 A1 | 5/2008 | Treacy |
| 2008/0125748 A1 | 5/2008 | Patel |
| 2008/0132850 A1 | 6/2008 | Fumiyama et al. |
| 2008/0262430 A1 | 10/2008 | Anderson et al. |
| 2008/0262431 A1 | 10/2008 | Anderson et al. |
| 2008/0294111 A1 | 11/2008 | Tal et al. |
| 2008/0312578 A1 | 12/2008 | DeFonzo et al. |
| 2008/0319387 A1 | 12/2008 | Amisar et al. |
| 2009/0187147 A1 | 7/2009 | Kurth et al. |
| 2009/0221961 A1 | 9/2009 | Tal et al. |
| 2009/0270889 A1 | 10/2009 | Tal et al. |
| 2009/0292272 A1 | 11/2009 | McKinnon |
| 2010/0030154 A1 | 2/2010 | Duffy |
| 2010/0256487 A1 | 10/2010 | Hawkins et al. |
| 2010/0298839 A1 | 11/2010 | Castro |
| 2010/0305474 A1 | 12/2010 | DeMars et al. |
| 2011/0004162 A1 | 1/2011 | Tal |
| 2011/0009827 A1 | 1/2011 | Bierman et al. |
| 2011/0021994 A1 | 1/2011 | Anderson et al. |
| 2011/0066142 A1 | 3/2011 | Tal et al. |
| 2011/0071502 A1 | 3/2011 | Asai |
| 2011/0144620 A1 | 6/2011 | Tal |
| 2011/0152836 A1 | 6/2011 | Riopelle et al. |
| 2011/0202006 A1 | 8/2011 | Bierman et al. |
| 2011/0251559 A1 | 10/2011 | Tal et al. |
| 2011/0270192 A1 | 11/2011 | Anderson et al. |
| 2012/0041371 A1 | 2/2012 | Tal et al. |
| 2012/0065590 A1 | 3/2012 | Bierman et al. |
| 2012/0078231 A1 | 3/2012 | Hoshinouchi |
| 2012/0130411 A1 | 5/2012 | Tal et al. |
| 2012/0130415 A1 | 5/2012 | Tal et al. |
| 2012/0157854 A1 | 6/2012 | Kurrus et al. |
| 2012/0215171 A1 | 8/2012 | Christiansen |
| 2012/0220942 A1 | 8/2012 | Hall et al. |
| 2012/0226239 A1 | 9/2012 | Green |
| 2012/0283640 A1 | 11/2012 | Anderson et al. |
| 2012/0316500 A1 | 12/2012 | Bierman et al. |
| 2013/0053763 A1 | 2/2013 | Makino et al. |
| 2013/0053826 A1 | 2/2013 | Shevgoor |
| 2013/0123704 A1 | 5/2013 | Bierman et al. |
| 2013/0158338 A1 | 6/2013 | Kelly et al. |
| 2013/0188291 A1 | 7/2013 | Vardiman |
| 2013/0237931 A1 | 9/2013 | Tal et al. |
| 2013/0306079 A1 | 11/2013 | Tracy |
| 2014/0025036 A1 | 1/2014 | Bierman et al. |
| 2014/0081210 A1 | 3/2014 | Bierman et al. |
| 2014/0094774 A1 | 4/2014 | Blanchard |
| 2014/0100552 A1 | 4/2014 | Gallacher et al. |
| 2014/0207052 A1 | 7/2014 | Tal et al. |
| 2014/0207069 A1 | 7/2014 | Bierman et al. |
| 2014/0214005 A1 | 7/2014 | Belson |
| 2014/0257111 A1 | 9/2014 | Yamashita et al. |
| 2014/0276432 A1 | 9/2014 | Bierman et al. |
| 2014/0276599 A1 | 9/2014 | Cully et al. |
| 2015/0011834 A1 | 1/2015 | Ayala et al. |
| 2015/0080939 A1 | 3/2015 | Adams et al. |
| 2015/0094653 A1 | 4/2015 | Pacheco et al. |
| 2015/0112307 A1 | 4/2015 | Margolis |
| 2015/0112310 A1 | 4/2015 | Call et al. |
| 2015/0126930 A1 | 5/2015 | Bierman et al. |
| 2015/0148595 A1 | 5/2015 | Bagwell et al. |
| 2015/0190168 A1 | 7/2015 | Bierman et al. |
| 2015/0196210 A1 | 7/2015 | McCaffrey et al. |
| 2015/0224287 A1 | 8/2015 | Bian et al. |
| 2015/0283357 A1 | 10/2015 | Lampropoulos et al. |
| 2015/0297868 A1 | 10/2015 | Tal et al. |
| 2015/0320969 A1 | 11/2015 | Haslinger et al. |
| 2015/0320977 A1 | 11/2015 | Vitullo et al. |
| 2015/0351793 A1 | 12/2015 | Bierman et al. |
| 2015/0359549 A1 | 12/2015 | Lenker et al. |
| 2015/0359998 A1 | 12/2015 | Carmel et al. |
| 2016/0082223 A1 | 3/2016 | Barnell |
| 2016/0114124 A1 | 4/2016 | Tal |
| 2016/0158523 A1 | 6/2016 | Helm |
| 2016/0220786 A1 * | 8/2016 | Mitchell ........... A61M 25/0606 |
| 2016/0242661 A1 | 8/2016 | Fischell et al. |
| 2016/0256101 A1 | 9/2016 | Aharoni et al. |
| 2016/0325073 A1 | 11/2016 | Davies et al. |
| 2016/0338728 A1 | 11/2016 | Tal |
| 2016/0346503 A1 | 12/2016 | Jackson et al. |
| 2017/0035990 A1 | 2/2017 | Swift |
| 2017/0072165 A1 | 3/2017 | Lim et al. |
| 2017/0120000 A1 | 5/2017 | Osypka et al. |
| 2017/0120014 A1 | 5/2017 | Harding et al. |
| 2017/0120034 A1 | 5/2017 | Kaczorowski |
| 2017/0128700 A1 | 5/2017 | Roche Rebollo |
| 2017/0156987 A1 | 6/2017 | Babbs et al. |
| 2017/0172653 A1 | 6/2017 | Urbanski et al. |
| 2017/0182293 A1 | 6/2017 | Chhikara et al. |
| 2017/0239443 A1 | 8/2017 | Abitabilo et al. |
| 2017/0259043 A1 | 9/2017 | Chan et al. |

(56) References Cited

U.S. PATENT DOCUMENTS

| | | |
|---|---|---|
| 2017/0273713 A1 | 9/2017 | Shah et al. |
| 2017/0296792 A1 | 10/2017 | Ornelas Vargas et al. |
| 2017/0326339 A1 | 11/2017 | Bailey et al. |
| 2017/0361070 A1 | 12/2017 | Hivert |
| 2017/0368255 A1 | 12/2017 | Provost et al. |
| 2018/0001062 A1 | 1/2018 | O'Carrol et al. |
| 2018/0021545 A1 | 1/2018 | Mitchell et al. |
| 2018/0116690 A1 | 5/2018 | Sarabia et al. |
| 2018/0117284 A1 | 5/2018 | Appling et al. |
| 2018/0133438 A1 | 5/2018 | Hulvershorn et al. |
| 2018/0154062 A1 | 6/2018 | DeFonzo et al. |
| 2018/0154112 A1 | 6/2018 | Chan et al. |
| 2018/0214674 A1 | 8/2018 | Ebnet et al. |
| 2018/0296799 A1 | 10/2018 | Horst et al. |
| 2018/0296804 A1* | 10/2018 | Bierman ............ A61M 25/0693 |
| 2018/0310955 A1 | 11/2018 | Lindekugel et al. |
| 2019/0015646 A1 | 1/2019 | Matlock et al. |
| 2019/0021640 A1 | 1/2019 | Burkholz et al. |
| 2019/0060616 A1 | 2/2019 | Solomon |
| 2019/0076167 A1 | 3/2019 | Fantuzzi et al. |
| 2019/0134349 A1 | 5/2019 | Cohn et al. |
| 2019/0192824 A1 | 6/2019 | Cordeiro et al. |
| 2019/0201665 A1 | 7/2019 | Turpin |
| 2019/0209812 A1 | 7/2019 | Burkholz et al. |
| 2019/0255294 A1 | 8/2019 | Mitchell et al. |
| 2019/0255298 A1 | 8/2019 | Mitchell et al. |
| 2019/0275303 A1 | 9/2019 | Tran et al. |
| 2019/0276268 A1 | 9/2019 | Akingba |
| 2019/0321590 A1 | 10/2019 | Burkholz et al. |
| 2020/0001051 A1 | 1/2020 | Huang et al. |
| 2020/0016374 A1 | 1/2020 | Burkholz et al. |
| 2020/0046948 A1 | 2/2020 | Burkholz et al. |
| 2020/0100716 A1 | 4/2020 | Devgon et al. |
| 2020/0129732 A1 | 4/2020 | Vogt et al. |
| 2020/0147349 A1 | 5/2020 | Holt |
| 2020/0197682 A1* | 6/2020 | Franklin ............ A61M 25/0097 |
| 2020/0197684 A1 | 6/2020 | Wax |
| 2020/0237278 A1 | 7/2020 | Asbaghi |
| 2020/0359995 A1 | 11/2020 | Walsh et al. |
| 2021/0030944 A1 | 2/2021 | Cushen et al. |
| 2021/0060306 A1 | 3/2021 | Kumar |
| 2021/0069471 A1 | 3/2021 | Howell |
| 2021/0085927 A1 | 3/2021 | Howell |
| 2021/0100985 A1 | 4/2021 | Akcay et al. |
| 2021/0113809 A1 | 4/2021 | Howell |
| 2021/0113810 A1 | 4/2021 | Howell |
| 2021/0113816 A1 | 4/2021 | DiCianni |
| 2021/0121661 A1 | 4/2021 | Howell |
| 2021/0121667 A1 | 4/2021 | Howell |
| 2021/0228842 A1 | 7/2021 | Scherich et al. |
| 2021/0228843 A1 | 7/2021 | Howell et al. |
| 2021/0290898 A1 | 9/2021 | Burkholz |
| 2021/0290901 A1 | 9/2021 | Burkholz et al. |
| 2021/0290913 A1 | 9/2021 | Horst et al. |
| 2021/0322729 A1 | 10/2021 | Howell |
| 2021/0330941 A1 | 10/2021 | Howell et al. |
| 2021/0330942 A1 | 10/2021 | Howell |
| 2021/0361915 A1 | 11/2021 | Howell et al. |
| 2021/0402149 A1 | 12/2021 | Howell |
| 2022/0001138 A1 | 1/2022 | Howell |
| 2022/0032013 A1 | 2/2022 | Howell et al. |
| 2022/0032014 A1 | 2/2022 | Howell et al. |
| 2022/0062528 A1 | 3/2022 | Thornley et al. |
| 2022/0126064 A1 | 4/2022 | Tobin et al. |
| 2022/0193376 A1 | 6/2022 | Spataro et al. |
| 2022/0193377 A1 | 6/2022 | Haymond et al. |
| 2022/0193378 A1 | 6/2022 | Spataro et al. |
| 2022/0323723 A1 | 10/2022 | Spataro et al. |
| 2022/0331563 A1 | 10/2022 | Papadia |
| 2023/0042898 A1 | 2/2023 | Howell et al. |
| 2023/0096377 A1 | 3/2023 | West et al. |
| 2023/0096740 A1 | 3/2023 | Bechstein et al. |
| 2023/0099654 A1 | 3/2023 | Blanchard et al. |
| 2023/0100482 A1 | 3/2023 | Howell |
| 2023/0101455 A1 | 3/2023 | Howell et al. |
| 2023/0102231 A1 | 3/2023 | Bechstein et al. |
| 2023/0233814 A1 | 7/2023 | Howell et al. |
| 2024/0009427 A1 | 1/2024 | Howell et al. |
| 2024/0050706 A1 | 2/2024 | Howell et al. |
| 2024/0198058 A1 | 6/2024 | Howell et al. |

FOREIGN PATENT DOCUMENTS

| | | |
|---|---|---|
| EP | 0730880 A1 | 9/1996 |
| EP | 2061385 A1 | 5/2009 |
| EP | 1458437 B1 | 3/2010 |
| EP | 2248549 A2 | 11/2010 |
| EP | 2319576 A1 | 5/2011 |
| EP | 2366422 A1 | 9/2011 |
| EP | 2486880 A2 | 8/2012 |
| EP | 2486881 A2 | 8/2012 |
| EP | 2486951 A2 | 8/2012 |
| EP | 2512576 A2 | 10/2012 |
| EP | 2152348 B1 | 2/2015 |
| EP | 3473291 A1 | 4/2019 |
| EP | 3093038 B1 | 5/2019 |
| EP | 2260897 B1 | 9/2019 |
| EP | 3693051 A1 | 8/2020 |
| GB | 1273547 A | 5/1972 |
| JP | 2004248987 A | 9/2004 |
| JP | 2008054859 A | 3/2008 |
| WO | 94/21315 A1 | 9/1994 |
| WO | 95/32009 A2 | 11/1995 |
| WO | 98/44979 A1 | 10/1998 |
| WO | 98/53871 A1 | 12/1998 |
| WO | 99/12600 A1 | 3/1999 |
| WO | 99/26681 A1 | 6/1999 |
| WO | 00/06221 A1 | 2/2000 |
| WO | 0054830 A1 | 9/2000 |
| WO | 2003008020 A1 | 1/2003 |
| WO | 2003057272 A2 | 7/2003 |
| WO | 03/068073 A1 | 8/2003 |
| WO | 2003066125 A2 | 8/2003 |
| WO | 2005096778 A2 | 10/2005 |
| WO | 2006055288 A2 | 5/2006 |
| WO | 2006055780 A2 | 5/2006 |
| WO | 2007046850 A2 | 4/2007 |
| WO | 2008033983 A1 | 3/2008 |
| WO | 2008092029 A2 | 7/2008 |
| WO | 2008/131300 A2 | 10/2008 |
| WO | 2008131289 A2 | 10/2008 |
| WO | 2009114833 A1 | 9/2009 |
| WO | 2009114837 A2 | 9/2009 |
| WO | 2010/048449 A2 | 4/2010 |
| WO | 2010056906 A2 | 5/2010 |
| WO | 2010083467 A2 | 7/2010 |
| WO | 2010/132608 A2 | 11/2010 |
| WO | 2011081859 A2 | 7/2011 |
| WO | 2011097639 A2 | 8/2011 |
| WO | 2011109792 A1 | 9/2011 |
| WO | 2011146764 A1 | 11/2011 |
| WO | 2012068162 A2 | 5/2012 |
| WO | 2012068166 A2 | 5/2012 |
| WO | 2012135761 A1 | 10/2012 |
| WO | 2012/154277 A1 | 11/2012 |
| WO | 2012162677 A1 | 11/2012 |
| WO | 2013026045 A1 | 2/2013 |
| WO | 2013138519 A1 | 9/2013 |
| WO | 2014006403 A1 | 1/2014 |
| WO | 2014/100392 A1 | 6/2014 |
| WO | 2014113257 A2 | 7/2014 |
| WO | 2014152005 A2 | 9/2014 |
| WO | 2014197614 A2 | 12/2014 |
| WO | 2015057766 A1 | 4/2015 |
| WO | 2015077560 A1 | 5/2015 |
| WO | 2015/168655 A2 | 11/2015 |
| WO | 2016110824 A1 | 7/2016 |
| WO | 2016123278 A1 | 8/2016 |
| WO | 2016139590 A1 | 9/2016 |
| WO | 2016139597 A2 | 9/2016 |
| WO | 2016/178974 A1 | 11/2016 |
| WO | 2016/187063 A1 | 11/2016 |
| WO | 2016176065 A1 | 11/2016 |
| WO | 2018089275 A1 | 5/2018 |

(56) References Cited

FOREIGN PATENT DOCUMENTS

| | | | |
|---|---|---|---|
| WO | 2018089285 | A1 | 5/2018 |
| WO | 2018089385 | A1 | 5/2018 |
| WO | 2018191547 | A1 | 10/2018 |
| WO | 2018213148 | A1 | 11/2018 |
| WO | 2018218236 | A1 | 11/2018 |
| WO | 2019/050576 | A1 | 3/2019 |
| WO | 2019/146026 | A1 | 8/2019 |
| WO | 2019199734 | A1 | 10/2019 |
| WO | 2020014149 | A1 | 1/2020 |
| WO | 2020069395 | A1 | 4/2020 |
| WO | 2020/109448 | A1 | 6/2020 |
| WO | 2020/113123 | A1 | 6/2020 |
| WO | 2021050302 | A1 | 3/2021 |
| WO | 2021/077103 | A1 | 4/2021 |
| WO | 2021062023 | A1 | 4/2021 |
| WO | 2021081205 | A1 | 4/2021 |
| WO | 2021086793 | A1 | 5/2021 |
| WO | 2021/236950 | A1 | 11/2021 |
| WO | 2022/031618 | A1 | 2/2022 |
| WO | 2022/094141 | A1 | 5/2022 |
| WO | 2022/133297 | A1 | 6/2022 |
| WO | 2022-140406 | A1 | 6/2022 |
| WO | 2022/140429 | A1 | 6/2022 |
| WO | 2022/217098 | A1 | 10/2022 |
| WO | 2023014994 | A1 | 2/2023 |
| WO | 2023049498 | A1 | 3/2023 |
| WO | 2023049505 | A1 | 3/2023 |
| WO | 2023049511 | A1 | 3/2023 |
| WO | 2023049519 | A1 | 3/2023 |
| WO | 2023049522 | A1 | 3/2023 |
| WO | 2023146792 | A1 | 8/2023 |

OTHER PUBLICATIONS

PCT/US2021/057135 filed Oct. 28, 2021 International Search Report and Written Opinion dated Mar. 11, 2022.
PCT/US2023/011173 filed Jan. 19, 2023 International Search Report and Written Opinion dated May 22, 2023.
U.S. Appl. No. 17/237,909, filed Apr. 22, 2021 Non-Final Office Action dated Jul. 27, 2023.
U.S. Appl. No. 17/240,591, filed Apr. 26, 2021 Non-Final Office Action dated Jun. 8, 2023.
U.S. Appl. No. 17/326,017, filed May 20, 2021 Notice of Allowance dated Jul. 3, 2023.
U.S. Appl. No. 17/360,694, filed Jun. 28, 2021 Restriction Requirement dated Jul. 20, 2023.
U.S. Appl. No. 17/390,682, filed Jul. 30, 2021 Final Office Action dated Jul. 27, 2023.
U.S. Appl. No. 17/392,061, filed Aug. 2, 2021 Non-Final Office Action dated Jul. 17, 2023.
PCT/US2022/039614 filed Aug. 5, 2022 International Search Report and Written Opinion dated Dec. 22, 2022.
PCT/US2022/044848 filed Sep. 27, 2022 International Search Report and Written Opinion dated Feb. 3, 2023.
PCT/US2022/044879 filed Sep. 27, 2022 International Search Report and Written Opinion dated Mar. 3, 2023.
PCT/US2022/044901 filed Sep. 27, 2022 International Search Report and Written Opinion dated Mar. 3, 2023.
PCT/US2022/044918 filed Sep. 27, 2022 International Search Report and Written Opinion dated Feb. 21, 2023.
PCT/US2022/044923 filed Sep. 27, 2022 International Search Report and Written Opinion dated Feb. 15, 2023.
U.S. Appl. No. 17/156,252, filed Jan. 22, 2021 Notice of Allowance dated Apr. 24, 2023.
U.S. Appl. No. 17/237,909, filed Apr. 22, 2021 Restriction Requirement dated Feb. 1, 2023.
U.S. Appl. No. 17/326,017, filed May 20, 2021 Non-Final Office Action dated Jan. 26, 2023.
U.S. Appl. No. 17/390,682, filed Jul. 30, 2021 Non-Final Office Action dated Mar. 2, 2023.
U.S. Appl. No. 17/392,061, filed Aug. 2, 2021 Restriction Requirement dated Mar. 30, 2023.
PCT/US2021/028018 filed Apr. 19, 2021 International Preliminary Report on Patentability dated Jun. 3, 2022.
PCT/US2021/064174 filed Dec. 17, 2021 International Search Report and Written Opinion dated May 18, 2022.
PCT/US2021/064642 filed Dec. 21, 2021 International Search Report and Written Opinion dated May 11, 2022.
PCT/US2021/064671 filed Dec. 21, 2021 International Search Report and Written Opinion dated May 27, 2022.
PCT/US2022/024085 filed Apr. 8, 2022 International Search Report and Wirtten Opinion dated Sep. 12, 2022.
U.S. Appl. No. 16/398,020, filed Apr. 29, 2019 Examiner's Answer dated Oct. 31, 2022.
U.S. Appl. No. 17/031,478, filed Sep. 24, 2020 Notice of Allowance dated Sep. 16, 2022.
U.S. Appl. No. 17/156,252, filed Jan. 22, 2021 Non-Final Office Action dated Oct. 25, 2022.
PCT/US2021/039084 filed Jun. 25, 2021 International Search Report and Written Opinion dated Jan. 10, 2022.
PCT/US2021/039843 filed Jun. 30, 2021 International Search Report and Written Opinion dated Nov. 11, 2021.
PCT/US2021/044029 filed Jul. 30, 2021 International Search Report and Written Opinion dated Dec. 9, 2021.
U.S. Appl. No. 16/398,020, filed Apr. 29, 2019 Final Office Action dated Jan. 25, 2022.
U.S. Appl. No. 17/077,728, filed Oct. 29, 2020 Non-Final Office Action dated Feb. 9, 2022.
PCT/US2021/044223 filed Aug. 2, 2021 International Search Report and Written Opinion dated Dec. 21, 2021.
PCT/US2021/048275 filed Aug. 30, 2021 International Search Report and Written Opinion dated Jan. 4, 2022.
U.S. Appl. No. 17/031,478, filed Sep. 24, 2020 Non-Final Office Action dated May 11, 2022.
PCT/US2021/028018 filed Apr. 19, 2021 International Search Report and Written Opinion dated Sep. 13, 2021.
PCT/US2021/028683 filed Apr. 22, 2021 International Search Report and Written Opinion dated Sep. 16, 2021.
PCT/US2021/029183 filed Apr. 26, 2021 International Search Report and Written Opinion dated Sep. 24, 2021.
PCT/US2021/033443 filed May 20, 2021 International Search Report and Written Opinion dated Sep. 23, 2021.
U.S. Appl. No. 16/398,020, filed Apr. 29, 2019 Board Decision dated Oct. 30, 2023.
U.S. Appl. No. 17/156,252, filed Jan. 22, 2021 Notice of Allowance dated Aug. 9, 2023.
U.S. Appl. No. 17/237,909, filed Apr. 22, 2021 Notice of Allowance dated Oct. 27, 2023.
U.S. Appl. No. 17/240,591, filed Apr. 26, 2021 Final Office Action dated Dec. 6, 2023.
U.S. Appl. No. 17/360,694, filed Jun. 28, 2021 Non-Final Office Action dated Oct. 13, 2023.
U.S. Appl. No. 17/390,682, filed Jul. 30, 2021 Non-Final Office Action dated Dec. 1, 2023.
U.S. Appl. No. 17/392,061, filed Aug. 2, 2021 Final Office Action dated Nov. 21, 2023.
U.S. Appl. No. 17/513,789, filed Oct. 28, 2021 Restriction Requirement dated Oct. 3, 2023.
U.S. Appl. No. 17/557,924, filed Dec. 21, 2021 Non-Final Office Action dated Nov. 3, 2023.
PCT/US2020/048583 filed Aug. 28, 2020 International Search Report and Written Opinion dated Nov. 13, 2020.
PCT/US2020/052536 filed Sep. 24, 2020 International Search Report and Written Opinion dated Dec. 4, 2020.
PCT/US2020/056364 filed Oct. 19, 2020 International Search Report and Written Opinion dated Jan. 19, 2021.
PCT/US2020/056864 filed Oct. 22, 2020 International Search Report and Written Opinion dated Jan. 14, 2021.
PCT/US2020/057202 filed Oct. 23, 2020 International Search Report and Written Opinion dated Jan. 21, 2021.
PCT/US2020/057397 filed Oct. 26, 2020 International Search Report and Written Opinion dated Mar. 10, 2021.

(56) References Cited

OTHER PUBLICATIONS

PCT/US2021/014700 filed Jan. 22, 2021 International Search Report and Written Opinion dated Jun. 29, 2021.
U.S. Appl. No. 15/008,628, filed Jan. 28, 2016 Final Office Action dated May 30, 2018.
U.S. Appl. No. 15/008,628, filed Jan. 28, 2016 Non-Final Office Action dated Jan. 25, 2019.
U.S. Appl. No. 15/008,628, filed Jan. 28, 2016 Non-Final Office Action dated Nov. 2, 2017.
U.S. Appl. No. 15/008,628, filed Jan. 28, 2016 Notice of Allowance dated May 15, 2019.
U.S. Appl. No. 16/398,020, filed Apr. 29, 2019 Non-Final Office Action dated May 11, 2021.
U.S. Appl. No. 16/398,020, filed Apr. 29, 2019 Non-Final Office Action dated Jan. 18, 2024.
U.S. Appl. No. 17/234,611, filed Apr. 19, 2021 Restriction Requirement dated Jan. 18, 2024.
U.S. Appl. No. 17/240,591, filed Apr. 26, 2021 Advisory Action dated Feb. 22, 2024.
U.S. Appl. No. 17/360,694, filed Jun. 28, 2021 Non-Final Office Action dated Feb. 14, 2024.
U.S. Appl. No. 17/392,061, filed Aug. 2, 2021 Advisory Action dated Feb. 14, 2024.
U.S. Appl. No. 17/557,924, filed Dec. 21, 2021 Final Office Action dated Feb. 29, 2024.
U.S. Appl. No. 16/398,020, filed Apr. 29, 2019 Notice of Allowance dated May 20, 2024.
U.S. Appl. No. 17/234,611, filed Apr. 19, 2021 Non-Final Office Action dated Apr. 23, 2024.
U.S. Appl. No. 17/240,591, filed Apr. 26, 2021 Non-Final Office Action dated Jun. 4, 2024.
U.S. Appl. No. 17/390,682, filed Jul. 30, 2021 Final Office Action dated May 6, 2024.
U.S. Appl. No. 17/390,682, filed Jul. 30, 2021 Non-Final Office Action dated Jul. 5, 2024.
U.S. Appl. No. 17/392,061, filed Aug. 2, 2021 Non-Final Office Action dated Apr. 23, 2024.
U.S. Appl. No. 17/513,789, filed Oct. 28, 2021 Final Office Action dated Jul. 9, 2024.
U.S. Appl. No. 17/554,978, filed Dec. 17, 2021 Non-Final Office Action dated Apr. 19, 2024.
U.S. Appl. No. 17/240,591, filed Apr. 26, 2021 Final Office Action dated Aug. 14, 2024.
U.S. Appl. No. 17/554,978, filed Dec. 17, 2021 Notice of Allowance dated Jul. 24, 2024.
U.S. Appl. No. 17/557,924, filed Dec. 21, 2021 Non-Final Office Action dated Aug. 20, 2024.

* cited by examiner

RAPIDLY INSERTABLE CENTRAL CATHETERS INCLUDING CATHETER ASSEMBLIES AND METHODS THEREOF

PRIORITY

This application claims the benefit of priority to U.S. Provisional Application No. 63/045,649, filed Jun. 29, 2020, which is incorporated by reference in its entirety into this application.

BACKGROUND

A central venous catheter ("CVC") is formed of a material having a relatively low durometer, which contributes to the CVC being compliant but lacking column strength for direct insertion. Due to the lack of column strength, CVCs are commonly introduced into patients and advanced through their vasculatures by way of the Seldinger technique. The Seldinger technique utilizes a number of steps and medical devices (e.g., a needle, a scalpel, a guidewire, an introducer sheath, a dilator, a CVC, etc.). While the Seldinger technique is effective, the number of steps is time consuming, handling the number of medical devices is awkward, and both of the foregoing can lead to patient trauma. In addition, there is a relatively high potential for touch contamination due to the number of medical devices that need to be interchanged during the number of steps of the Seldinger technique. As such, there is a need to reduce the number of steps and medical devices involved in introducing a catheter such as a CVC into a patient and advancing the catheter through a vasculature thereof.

Disclosed herein are rapidly insertable central catheters ("RICCs") including catheter assemblies and methods thereof that address the foregoing.

SUMMARY

Disclosed herein is a RICC assembly for direct insertion into a blood-vessel lumen of a patient. The RICC assembly includes, in some embodiments, a RICC, an introducer, and a coupling system. The RICC includes a catheter tube, a catheter hub, and one or more extension legs. The catheter tube includes a side aperture through a side of the catheter tube in a distal-end portion thereof. The side aperture opens into an introducing lumen of the catheter tube that extends from at least the side aperture to a distal end of the RICC. The catheter hub is coupled to a proximal-end portion of the catheter tube. Each extension leg of the one-or-more extension legs is coupled to the catheter hub by a distal-end portion thereof. The introducer includes an introducer needle. The introducer needle has a needle shaft that extends through the distal end of the RICC when the RICC assembly is in at least a ready-to-deploy state of the RICC assembly. The introducer is configured to be actuated with a single finger of a hand while holding a distal-end portion of the introducer between a thumb and another finger or fingers of the hand. The coupling system is configured to couple the RICC and the introducer together. The coupling system includes a distal coupler slidably attached to the catheter tube proximal of the side aperture.

In some embodiments, the catheter tube further includes a first section and a second section, wherein the side aperture is proximal of the first section of the catheter tube. The first section is formed of a first material and the second section of the catheter tube is formed of a second material. The first material has a first durometer, and the second material has a second durometer less than the first durometer. The catheter tube is thereby configured with both column strength and compliance for advancing the catheter tube into the blood-vessel lumen and through a vasculature of the patient.

In some embodiments, the needle shaft further extends through a longitudinal through hole of the distal coupler, through the side aperture of the catheter tube, and along the introducing lumen of the catheter tube before exiting through the distal end of the RICC when the RICC assembly is in at least the ready-to-deploy state thereof.

In some embodiments, the distal coupler includes a push tab configured to allow a clinician to single handedly advance the RICC off the needle shaft with the single finger of the hand while holding the distal-end portion of the introducer between the thumb and the other finger or fingers of the hand.

In some embodiments, the introducer further includes a syringe. The syringe includes a barrel, a plunger disposed in the barrel, and a syringe housing around the barrel. The barrel has a syringe tip in a distal-end portion thereof coupled to a needle hub of the introducer needle in at least the ready-to-deploy state of the RICC assembly. The syringe housing has a distal-end portion and a proximal-end portion. The proximal-end portion of the syringe housing is either integral with or coupled to a proximal-end portion of the plunger such that proximally sliding the syringe housing relative to the barrel withdraws the plunger from the barrel.

In some embodiments, the syringe further includes a push tab proximally extending over the barrel from the distal-end portion of the barrel to which the push tab is coupled. The push tab is configured for pushing against with the single finger while holding the distal-end portion of the syringe housing between the thumb and the other finger or fingers of the hand, which proximally slides the syringe housing relative to the barrel and withdraws the plunger from the barrel.

In some embodiments, the introducer further includes an access guidewire disposed in an access-guidewire lumen. The access-guidewire lumen is formed of at least a plunger lumen of the plunger and a needle lumen of the introducer needle. The access guidewire has a length sufficient for extension of the access guidewire through the distal end of the RICC and into the blood-vessel lumen of the patient.

In some embodiments, the plunger includes a sealing mechanism in a distal-end portion of the plunger for sealing off the access-guidewire lumen distal of the sealing mechanism. The sealing mechanism is configured to maintain a vacuum for aspirating blood when the plunger is withdrawn from the barrel.

In some embodiments, the syringe further includes a slider distally extending over the barrel from the syringe housing. The slider is configured for actuating the access guidewire with the single finger while holding the distal-end portion of the syringe housing between the thumb and the other finger or fingers of the hand. The slider includes an extension extending through a longitudinal slot in each of the barrel and the plunger into the access-guidewire lumen proximal of the sealing mechanism where the extension is coupled to the access guidewire.

In some embodiments, the introducer further includes a fluid-pressure indicator extending from a side arm of the needle hub. The fluid-pressure indicator is fluidly coupled to the needle lumen of the introducer needle by way of a side-arm lumen of the side arm for observing blood flashback due to an accidental arterial puncture.

In some embodiments, the coupling system further includes a proximal coupler coupled to the syringe and slidably attached to the catheter hub in at least the ready-to-deploy state of the RICC assembly. The coupling system is configured to allow the RICC to slide relative to the introducer.

In some embodiments, the proximal coupler includes a catheter-hub clip from which the RICC is configured to suspend by the catheter hub in at least the ready-to-deploy state of the RICC assembly. The RICC is configured to suspend from the catheter-hub clip by the one-or-more extension legs when the proximal coupler is advanced thereover in an operating state of the RICC assembly.

In some embodiments, the RICC further includes a collapsible catheter-tube sterile barrier over the catheter tube between the catheter hub and the distal coupler to which distal coupler the catheter-tube sterile barrier is coupled. The catheter-tube sterile barrier is configured to split apart when a sterile-barrier pull tab of the catheter-tube sterile barrier is removed from the catheter-hub clip and the catheter-tube sterile barrier is pulled away from the catheter tube by the sterile-barrier pull tab.

In some embodiments, the catheter-tube sterile barrier has sufficient tensile strength to pull the distal coupler off the catheter tube without breaking when the catheter-tube sterile barrier splits down to the distal coupler while being pulled away from the catheter tube.

In some embodiments, the RICC includes a set of three lumens including a primary lumen, a secondary lumen, and a tertiary lumen. The set of three lumens is formed of fluidly connected portions of three catheter-tube lumens, three hub lumens, and three extension-leg lumens. The introducing lumen of the catheter tube is coincident with a distal-end portion of the primary lumen.

In some embodiments, the primary lumen has a primary-lumen aperture in a distal end of the RICC, the secondary lumen has a secondary-lumen aperture in the side of the catheter tube distal of the side aperture, and the tertiary lumen has a tertiary-lumen aperture in the side of the catheter tube distal of the side aperture but proximal of the secondary-lumen aperture.

In some embodiments, the RICC further includes a maneuver guidewire disposed in the primary lumen. The maneuver guidewire has a length sufficient for extension of the maneuver guidewire to a lower ⅓ of a superior vena cava of a heart. The maneuver guidewire is captively disposed in the RICC by a stop about a proximal-end portion of the maneuver guidewire and a closed end of a fixed-length maneuver-guidewire sterile barrier coupled to a Luer connector. The stop provides a distal limit to advancing the maneuver guidewire. The closed end of the maneuver-guidewire sterile barrier around the maneuver guidewire provides a proximal limit to withdrawing the maneuver guidewire.

Also disclosed herein is a syringe. The syringe includes a barrel, a plunger disposed in the barrel, and a syringe housing around the barrel. The barrel has a syringe tip in a distal-end portion thereof. The syringe housing has a distal-end portion and a proximal-end portion. The proximal-end portion of the syringe housing is either integral with or coupled to a proximal-end portion of the plunger such that proximally sliding the syringe housing relative to the barrel withdraws the plunger from the barrel. The syringe configured to be actuated with a single finger of a hand while holding a distal-end portion of the syringe between a thumb and another finger or fingers of the hand.

In some embodiments, the syringe further includes a push tab proximally extending over the barrel from the distal-end portion of the barrel to which the push tab is coupled. The push tab is configured for pushing against with the single finger of the hand while holding the distal-end portion of the syringe housing between the thumb and the other finger or fingers of the hand, which proximally slides the syringe housing relative to the barrel and withdraws the plunger from the barrel.

In some embodiments, the syringe further includes an access guidewire disposed in an access-guidewire lumen. The access-guidewire lumen is formed of at least a plunger lumen of the plunger. The access guidewire has a length sufficient for extension of the access guidewire through the syringe tip and into a blood-vessel lumen of a patient.

In some embodiments, the plunger includes a sealing mechanism in a distal-end portion of the plunger for sealing off the access-guidewire lumen distal of the sealing mechanism. The sealing mechanism is configured to maintain a vacuum for aspirating blood when the plunger is withdrawn from the barrel.

In some embodiments, the syringe further includes a slider distally extending over the barrel from the syringe housing. The slider is configured for actuating the access guidewire with the single finger while holding the distal-end portion of the syringe housing between the thumb and the other finger or fingers of the hand. The slider includes an extension extending through a longitudinal slot in each of the barrel and the plunger into the access-guidewire lumen proximal of the sealing mechanism where the extension is coupled to the access guidewire.

Also disclosed herein is a method for inserting a RICC into a blood-vessel lumen of a patient. The method includes a RICC assembly-obtaining step, a needle tract-establishing step, a first RICC-advancing step, and a needle-withdrawing step. The RICC assembly-obtaining step includes obtaining a RICC assembly. The RICC assembly includes the RICC, an introducer including a syringe coupled to an introducer needle, and a coupling system including a distal coupler that couples the RICC and the introducer together by distal-end portions thereof in at least a ready-to-deploy state of the RICC assembly. The needle tract-establishing step includes establishing a needle tract from an area of skin to the blood-vessel lumen of the patient with a needle shaft of the introducer needle while holding a distal-end portion of a syringe housing around a barrel of the syringe between a thumb and another finger or fingers of a hand. Meanwhile, at least a single finger of the hand is kept readily available. The needle shaft extends through a longitudinal through hole of the distal coupler, through a side aperture in a distal-end portion of a catheter tube of the RICC, along an introducing lumen of the catheter tube, and out a distal end of the RICC for establishing the needle tract. The first RICC-advancing step includes advancing a distal-end portion of a first section of the catheter tube into the blood-vessel lumen over the needle shaft. The needle-withdrawing step includes withdrawing the needle shaft from the introducing lumen by way of the side aperture of the catheter tube.

In some embodiments, the method further includes a blood-aspirating step. The blood-aspirating step includes aspirating blood with the syringe to confirm a needle tip is disposed in the blood-vessel lumen of the patient before the needle-withdrawing step. The blood-aspirating step includes pushing a push tab extending over the barrel from a distal-end portion thereof with the single finger of the hand while holding the distal-end portion of the syringe housing between the thumb and the other finger or fingers of the hand, which proximally slides the syringe housing relative to the barrel and withdraws a syringe housing-connected plunger from the barrel.

In some embodiments, the first RICC-advancing step includes advancing the catheter tube into the blood-vessel lumen by a push tab of the distal coupler with the single finger of the hand while holding the distal-end portion of the syringe housing around a barrel of the syringe between the thumb and the other finger or fingers of the hand.

In some embodiments, the first RICC-advancing step includes advancing a catheter hub of the RICC from a catheter-hub clip of a proximal coupler of the coupling system and, thereafter, one or more extension legs of the RICC within the catheter-hub clip. The RICC is configured to suspend from the coupling system until at least withdrawing the needle shaft from both the introducing lumen and the longitudinal through hole of the distal coupler.

In some embodiments, the method further includes an access guidewire-advancing step. The access guidewire-advancing step includes advancing an access guidewire disposed in an access-guidewire lumen formed of at least a plunger lumen of the syringe and a needle lumen of the introducer needle into the blood-vessel lumen beyond a needle tip of the introducer needle. The access guidewire-advancing step is performed before the first RICC-advancing step. The access guidewire-advancing step includes distally advancing a slider coupled to the access guidewire over the barrel with the single finger while holding the distal-end portion of the syringe housing between the thumb and the other finger or fingers of the hand.

In some embodiments, the method further includes a maneuver guidewire-advancing step. The maneuver guidewire-advancing step includes advancing a maneuver guidewire into the blood-vessel lumen by way of a primary lumen having a primary-lumen aperture in the distal end of the RICC. The introducing lumen of the catheter tube is coincident with a distal-end portion of the primary lumen, thereby mandating the needle-withdrawing step before the maneuver guidewire-advancing step.

In some embodiments, the method further includes a second RICC-advancing step. The second RICC-advancing step includes advancing the distal-end portion of the first section of catheter tube farther into the blood-vessel lumen over the maneuver guidewire, which concomitantly includes sliding the distal coupler proximally toward a proximal-end portion of the catheter tube to uncover the catheter tube. The catheter tube is covered by a collapsible sterile barrier between the proximal-end portion of the catheter tube and the distal coupler in at least the ready-to-deploy state of the RICC assembly.

In some embodiments, the method further includes a sterile barrier-removing step. The sterile barrier-removing step includes removing the sterile barrier and the distal coupler from the RICC by pulling a sterile-barrier pull tab of the sterile barrier opposite the distal coupler away from the catheter tube to split the sterile barrier apart, then pulling the distal coupler from the catheter tube by the sterile barrier to which the distal coupler is slidably attached.

In some embodiments, the method further includes a sterile barrier-removing step. The sterile barrier-removing step includes removing the distal coupler and the sterile barrier from the RICC by pulling the distal coupler away from the catheter tube to split the sterile barrier apart, then pulling the distal coupler further proximally toward the proximal-end portion of the catheter tube to completely remove the sterile barrier.

These and other features of the concepts provided herein will become more apparent to those of skill in the art in view of the accompanying drawings and following description, which describe particular embodiments of such concepts in greater detail.

DRAWINGS

DESCRIPTION

Figure 1:
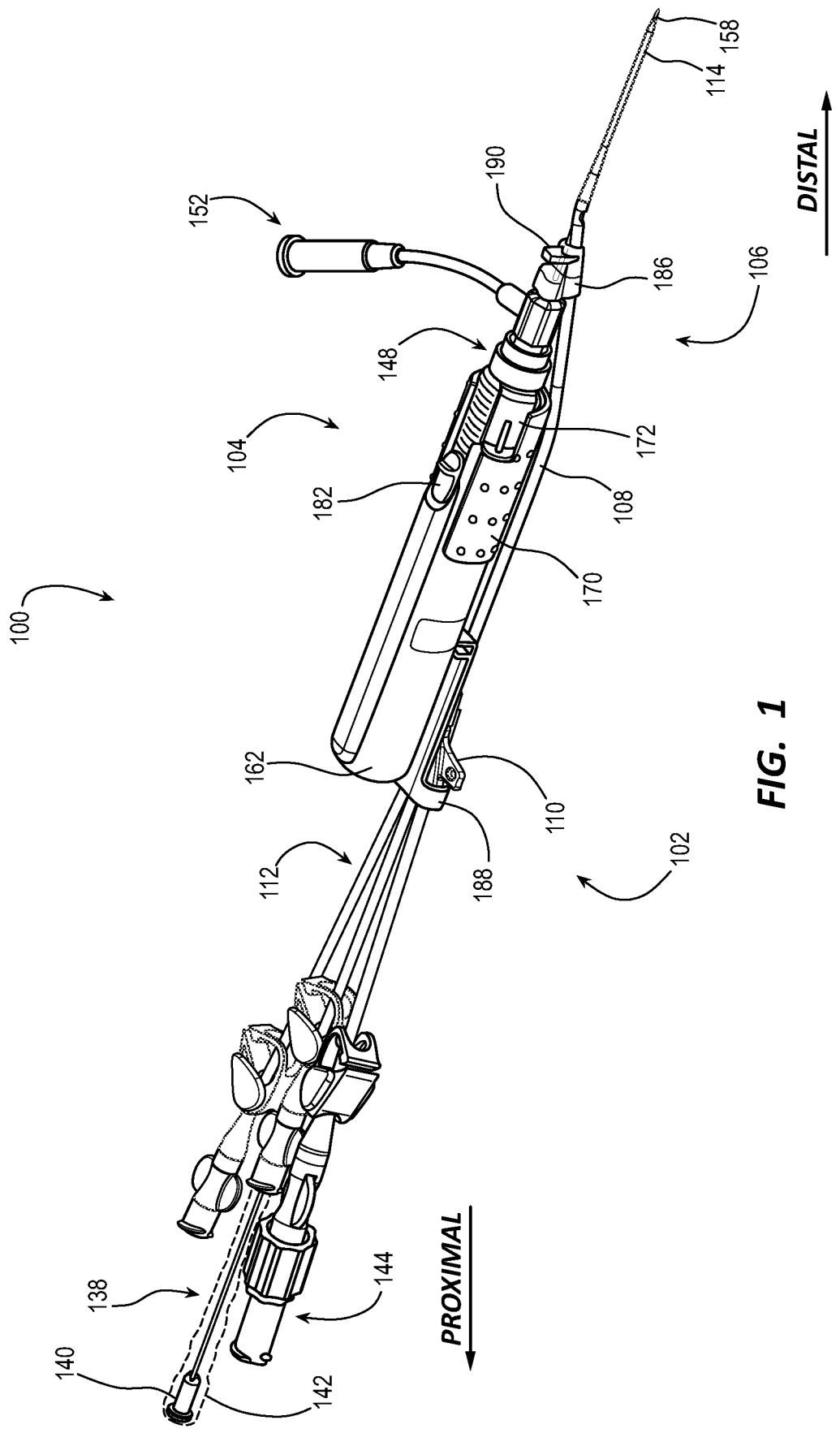
FIG. 1 illustrates an oblique view of a RICC assembly including a RICC, an introducer, and a coupling system in accordance with some embodiments.

Before some particular embodiments are disclosed in greater detail, it should be understood that the particular embodiments disclosed herein do not limit the scope of the concepts provided herein. It should also be understood that a particular embodiment disclosed herein can have features that can be readily separated from the particular embodiment and optionally combined with or substituted for features of any of a number of other embodiments disclosed herein.

Regarding terms used herein, it should also be understood the terms are for the purpose of describing some particular embodiments, and the terms do not limit the scope of the concepts provided herein. Ordinal numbers (e.g., first, second, third, etc.) are generally used to distinguish or identify different features or steps in a group of features or steps, and do not supply a serial or numerical limitation. For example, "first," "second," and "third" features or steps need not necessarily appear in that order, and the particular embodiments including such features or steps need not necessarily be limited to the three features or steps. Labels such as "left," "right," "top," "bottom," "front," "back," and the like are used for convenience and are not intended to imply, for example, any particular fixed location, orientation, or direction. Instead, such labels are used to reflect, for example, relative location, orientation, or directions. Singular forms of "a," "an," and "the" include plural references unless the context clearly dictates otherwise.

With respect to "proximal," a "proximal portion" or a "proximal-end portion" of, for example, a catheter disclosed herein includes a portion of the catheter intended to be near a clinician when the catheter is used on a patient. Likewise, a "proximal length" of, for example, the catheter includes a length of the catheter intended to be near the clinician when the catheter is used on the patient. A "proximal end" of, for example, the catheter includes an end of the catheter intended to be near the clinician when the catheter is used on the patient. The proximal portion, the proximal-end portion, or the proximal length of the catheter can include the proximal end of the catheter; however, the proximal portion, the proximal-end portion, or the proximal length of the catheter need not include the proximal end of the catheter. That is, unless context suggests otherwise, the proximal portion, the proximal-end portion, or the proximal length of the catheter is not a terminal portion or terminal length of the catheter.

With respect to "distal," a "distal portion" or a "distal-end portion" of, for example, a catheter disclosed herein includes a portion of the catheter intended to be near or in a patient when the catheter is used on the patient. Likewise, a "distal length" of, for example, the catheter includes a length of the catheter intended to be near or in the patient when the catheter is used on the patient. A "distal end" of, for example, the catheter includes an end of the catheter intended to be near or in the patient when the catheter is used on the patient. The distal portion, the distal-end portion, or the distal length of the catheter can include the distal end of the catheter; however, the distal portion, the distal-end portion, or the distal length of the catheter need not include the distal end of the catheter. That is, unless context suggests otherwise, the distal portion, the distal-end portion, or the distal length of the catheter is not a terminal portion or terminal length of the catheter.

Unless defined otherwise, all technical and scientific terms used herein have the same meaning as commonly understood by those of ordinary skill in the art.

As set forth above, there is a need to reduce the number of steps and medical devices involved in introducing a catheter such as a CVC into a patient and advancing the catheter through a vasculature thereof.

Disclosed herein are rapidly insertable central catheters ("RICCs"), RICC assemblies, and methods for direct insertion of such RICCs into a blood-vessel lumen of a patient. However, it should be understood the RICCs are but one type of catheter in which the concepts provided herein can be embodied or otherwise incorporated. Indeed, peripherally inserted central catheters ("PICCs"), dialysis catheters, or the like can also embody or otherwise incorporate the concepts provided herein for the RICCs, as well as catheter assemblies and methods thereof.

RICC Assemblies

Figure 2:
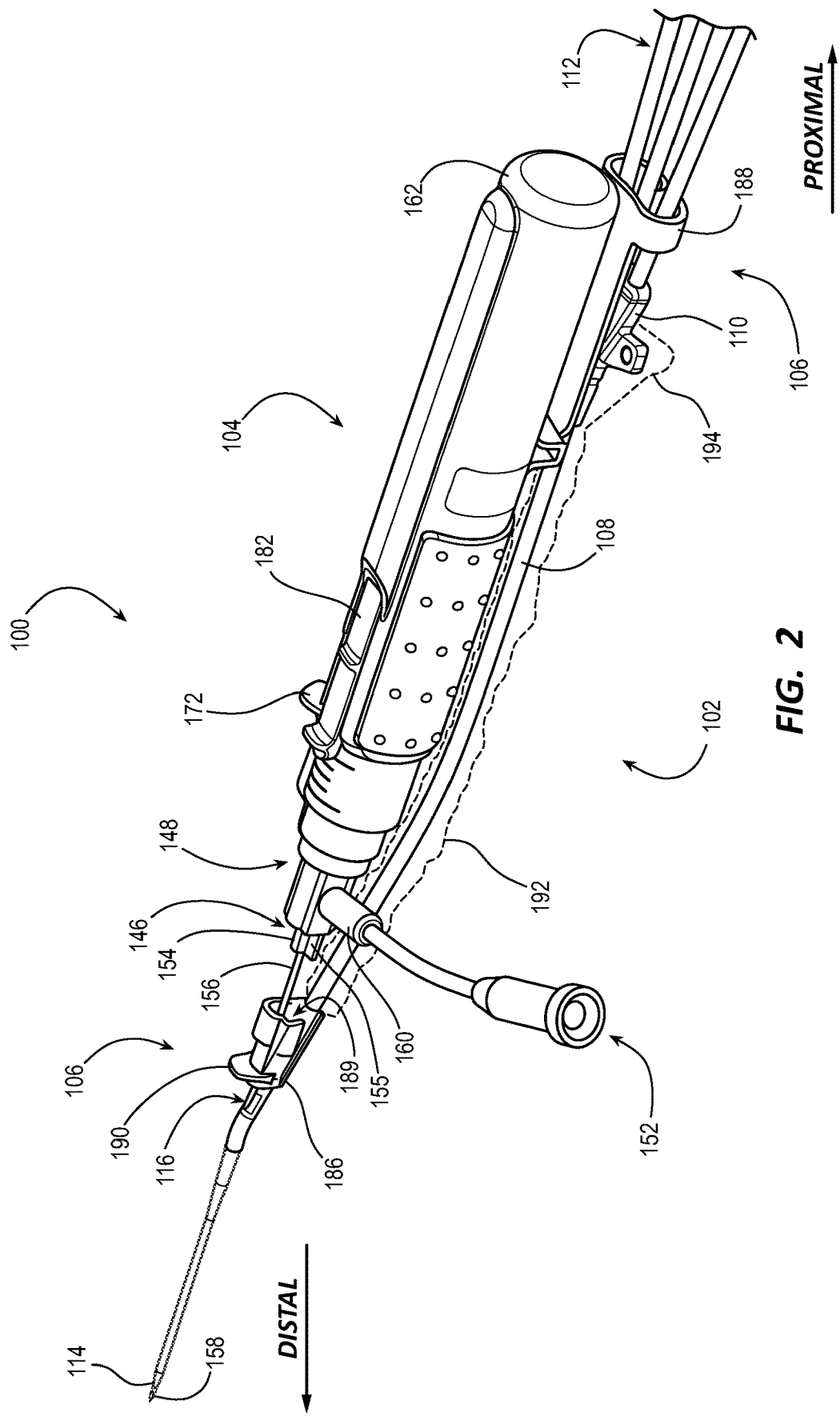
FIG. 2 illustrates a first detailed view of the RICC assembly in accordance with some embodiments.
Figure 3:
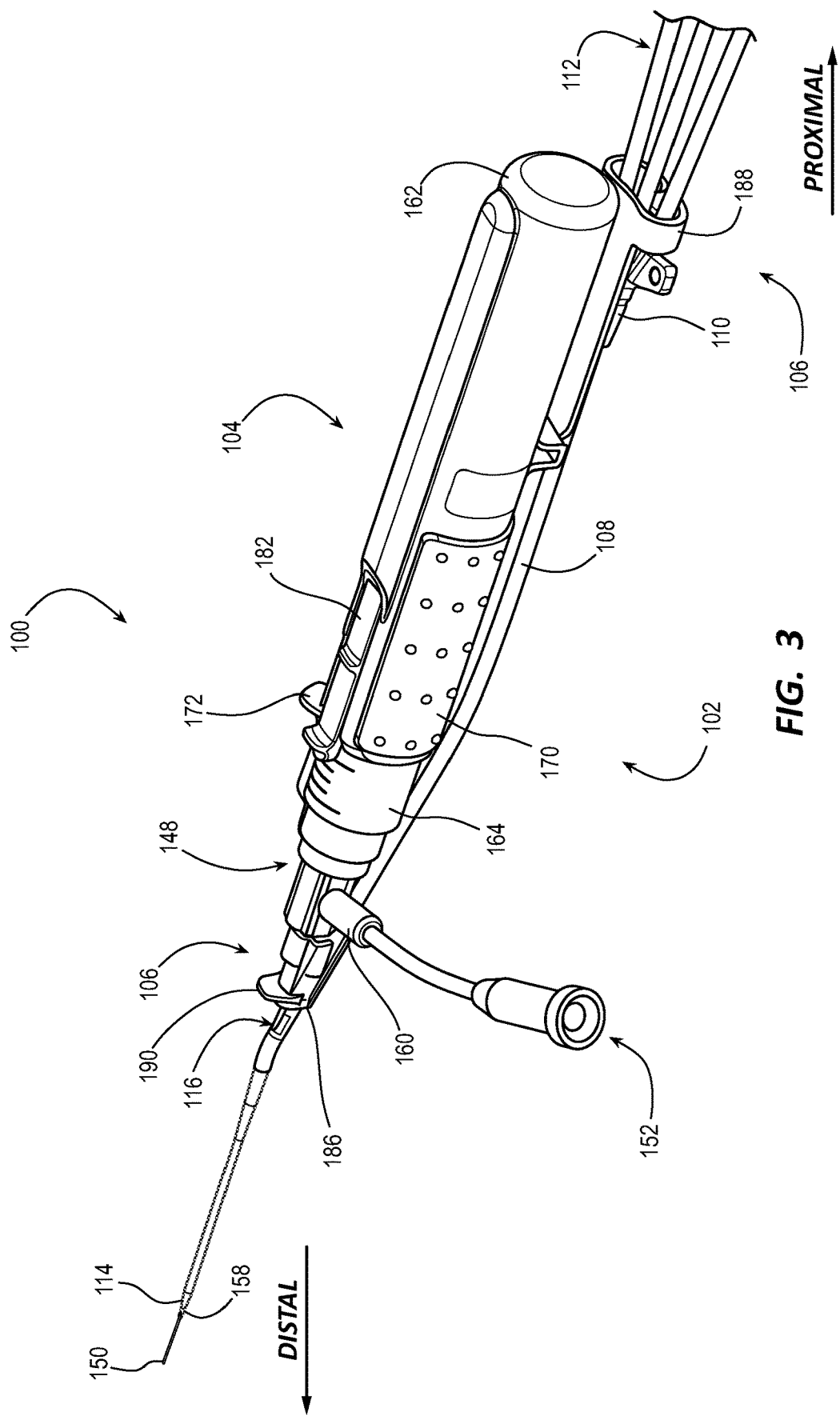
FIG. 3 illustrates a second detailed view of the RICC assembly in accordance with some embodiments.
Figure 4:
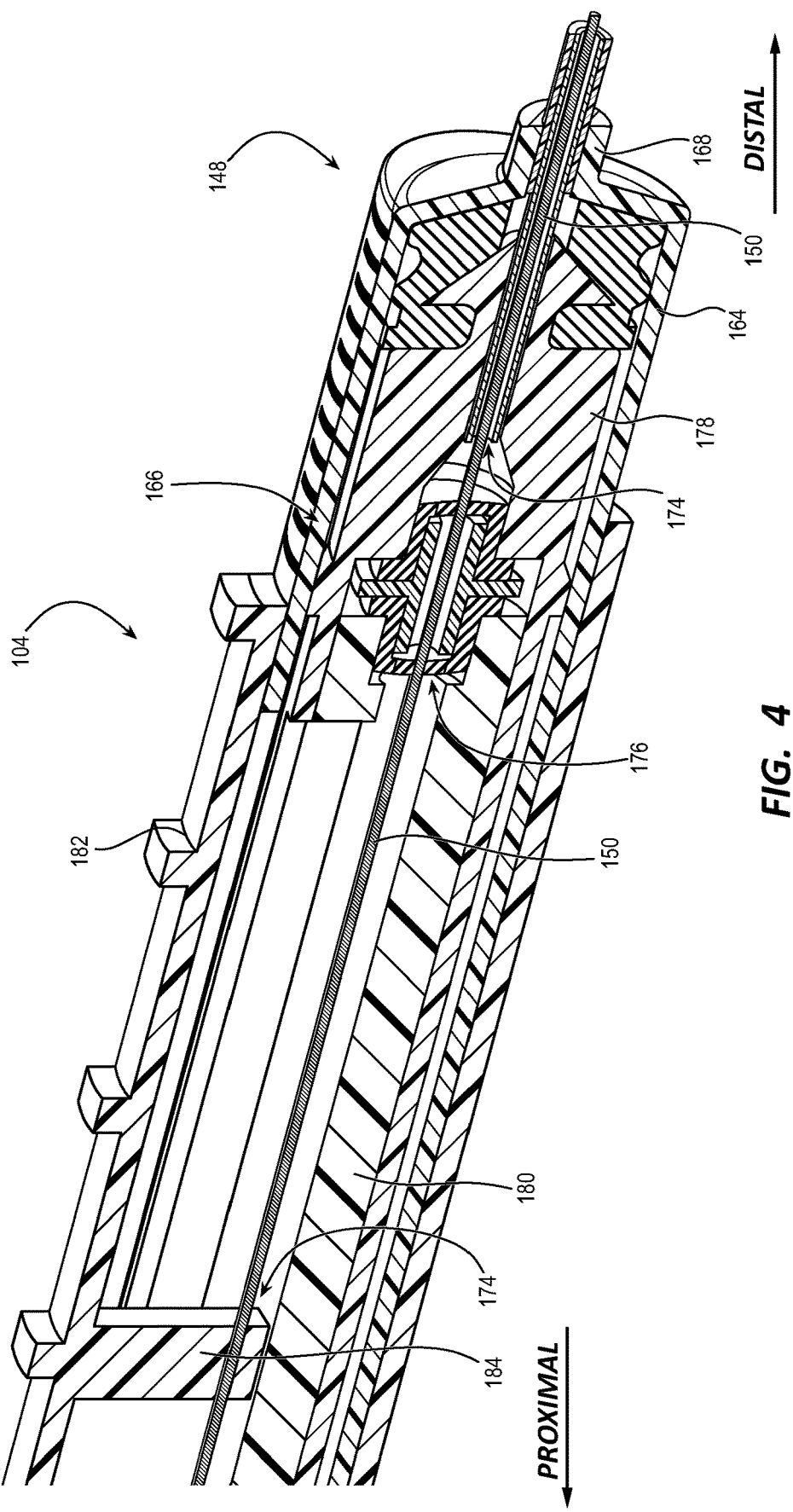
FIG. 4 illustrates a longitudinal cross section of a portion of the introducer in accordance with some embodiments.
Figure 5:
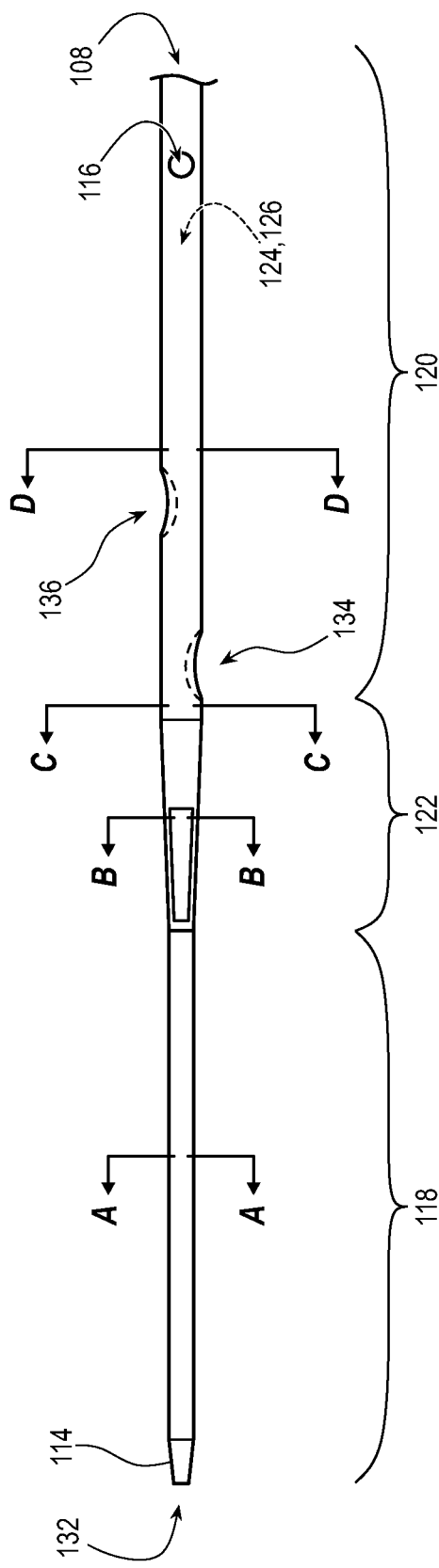
FIG. 5 illustrates a distal-end portion of a catheter tube of the RICC in accordance with some embodiments.
Figure 8:
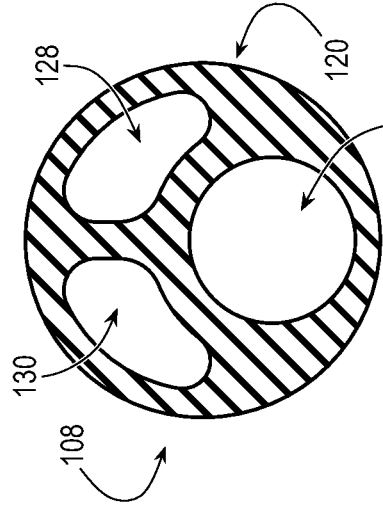
FIG. 8 illustrates a third or fourth transverse cross section of the catheter tube in accordance with some embodiments.
Figure 7:
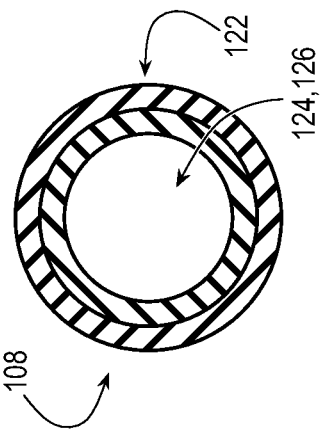
FIG. 7 illustrates a second transverse cross section of the catheter tube in accordance with some embodiments.
Figure 6:
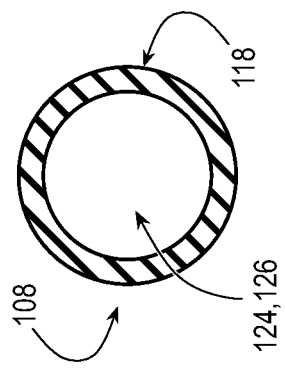
FIG. 6 illustrates a first transverse cross section of the catheter tube in accordance with some embodiments.

FIGS. 1-3 illustrate various views of a RICC assembly 100 including a RICC 102, an introducer 104, and a coupling system 106 in accordance with some embodiments. FIG. 4 illustrates a longitudinal cross section of a portion of the introducer 104 in accordance with some embodiments. FIG. 5 illustrates a distal-end portion of a catheter tube 108 of the RICC 102 in accordance with some embodiments. FIGS. 6-8 illustrate various transverse cross-sections of the catheter tube 108 in accordance with some embodiments.

As shown, the RICC assembly 100 includes, in some embodiments, the RICC 102, the introducer 104, and the coupling system 106 configured to couple the RICC 102 and the introducer 104 together. The RICC 102, the introducer 104, and the coupling system 106 are described, in turn, in sections set forth below; however, some crossover between the sections for the RICC 102, the introducer 104, and the coupling system 106 exist in view of the interrelatedness of the RICC 102, the introducer 104, and the coupling system 106 in the RICC assembly 100.

The RICC 102 includes the catheter tube 108, a catheter hub 110, and one or more extension legs 112.

The catheter tube 108 includes two or more sections including a catheter tip 114 in a distal-end portion of the catheter tube 108, one or more catheter-tube lumens, and a side aperture 116 through a side of the catheter tube 108 in the distal-end portion of the catheter tube 108.

The two or more sections of the catheter tube 108 can be a main body of the catheter tube 108 and the catheter tip 114, which can be formed as a single extruded piece of a single material or a single coextruded piece of two similar materials. Alternatively, the main body of the catheter tube 108 and the catheter tip 114 can be formed as two different extruded pieces of two similar materials and subsequently coupled. However, FIG. 5 illustrates an embodiment of the catheter tube 108 in which the catheter tube 108 is formed as two different extruded pieces of two different materials and subsequently coupled. Indeed, the catheter tube 108 includes a first section 118 including the catheter tip 114, a second section including the side aperture 116, and an optional transition section 122 therebetween depending upon the manner in which the first section 118 and the second section 120 of the catheter tube 108 are coupled. For example, the first and second sections 118 and 120 of the catheter tube 108 can be bonded by heat, solvent, or adhesive such that the first and second sections 118 and 120 abut each other, or the second section 120 can be inserted into the first section 118 and bonded thereto by heat, solvent, or adhesive, thereby forming the transition section 122. Advantageously, the latter coupling of inserting the second section 120 into the first section 118 facilitates incorporation of a smooth taper into the transition section 122, which taper is useful for dilation without catching tissue (e.g., skin) during methods of using the RICC assembly 100.

The first section 118 of the catheter tube 108 can be formed of a first material (e.g., a polymeric material such as polytetrafluoroethylene, polypropylene, or polyurethane) having a first durometer, while the second section 120 of the catheter tube 108 can be formed of a second material (e.g., a polymeric material such as polyvinyl chloride, polyethylene, polyurethane, or silicone) having a second durometer less than the first durometer. For example, each section of the first section 118 and the second section 120 of the catheter tube 108 can be made from a different polyurethane having a different durometer. Indeed, polyurethane is advantageous in that polyurethane sections of the catheter tube 108 can be relatively rigid at room-temperature but become more flexible in vivo at body temperature, which reduces irritation to vessel walls and phlebitis. Polyurethane is also advantageous in that can be less thrombogenic than some other polymers.

The catheter tube 108 having at least the first section 118 of the first polymeric material and the second section 120 of the second polymeric material has a column strength sufficient to prevent buckling of the catheter tube 108 when the catheter tube 108 is inserted into an insertion site, as well as a compliance suitable to advance the catheter tube 108 through a vasculature of a patient. Both the column strength and compliance of the catheter tube 108 is notable in that it makes it possible to rapidly insert the catheter tube 108 into the insertion site and advance the catheter tube 108 through the vasculature of the patient without using the Seldinger technique.

It should be understood the first durometer and the second durometer can be on different scales (e.g., Type A or Type D), so the second durometer of the second polymeric material might not be numerically less than the first durometer of the first polymeric material. That said, the hardness of the second polymeric material can still be less than the hardness of the first polymeric material as the different scales—each of which ranges from 0 to 100—are designed for characterizing different materials in groups of the materials having a like hardness.

Notwithstanding the foregoing, the first section 118 and the second section 120 of the catheter tube 108 can be formed of a same polymeric material or different polymeric materials having substantially equal durometers provided a) the column strength of the catheter tube 108 is sufficient to prevent buckling of the catheter tube 108 when inserted into an insertion site and b) the compliance of the catheter tube 108 is suitable to advance the catheter tube 108 through a vasculature of a patient.

The one-or-more catheter-tube lumens can extend through an entirety of the catheter tube 108; however, only one catheter-tube lumen typically extends from a proximal end of the catheter tube 108 to a distal end of the catheter tube 108 in a multiluminal RICC (e.g., a diluminal RICC, a triluminal RICC, a tetraluminal RICC, a pentaluminal RICC, a hexaluminal RICC, etc.). Indeed, the catheter tip 114 typically includes a single lumen therethrough. Optionally, the single lumen through the catheter tip 114 can be referred to as a "tip lumen," particularly in reference to the first section 118 of the catheter tube 108 when formed separately from a remainder of the catheter tube 108 and coupled thereto.

Again, the side aperture 116 is through the side of the catheter tube 108 in the distal-end portion of the catheter tube 108; however, the side aperture 116 is proximal of the first section 118 of the catheter tube 108. The side aperture 116 opens into an introducing lumen 124 of the one-or-more catheter-tube lumens. The introducing lumen 124 extends from at least the side aperture 116 in the second section 120 of the catheter tube 108, through the first section 118 of the catheter tube 108 distal thereof, and to a distal end of the RICC 102 (e.g., the distal end of the catheter tube 108 or a distal end of the catheter tip 114). The introducing lumen 124 is coincident with a distal-end portion of the one catheter-tube lumen set forth above that typically extends from the proximal end of the catheter tube 108 to the distal end of the catheter tube 108, particularly the distal-end portion of the foregoing catheter-tube lumen distal of the side aperture 116.

The catheter hub 110 is coupled to a proximal-end portion of the catheter tube 108. The catheter hub 110 includes one or more catheter-hub lumens corresponding in number to the one-or-more catheter-tube lumens. The one-or-more catheter-hub lumens extend through an entirety of the catheter hub 110 from a proximal end of the catheter hub 110 to a distal end of the catheter hub 110.

Each extension leg of the one-or-more extension legs 112 is coupled to the catheter hub 110 by a distal-end portion thereof. The one-or-more extension legs 112 respectively include one or more extension-leg lumens, which, in turn, correspond in number to the one-or-more catheter-tube lumens. Each extension-leg lumen of the one-or-more extension-leg lumens extends through an entirety of the extension leg from a proximal end of the extension leg to a distal end of the extension leg.

Each extension leg of the one-or-more extension legs 112 typically includes a Luer connector coupled to the extension leg, through which Luer connector the extension leg and the extension-leg lumen thereof can be connected to another medical device.

While the RICC 102 can be a monoluminal or multiluminal RICC (e.g., a diluminal RICC, a triluminal RICC, a tetraluminal RICC, a pentaluminal RICC, a hexaluminal RICC, etc.), the RICC 102 shown in FIGS. 1-3 and 6-8 is triluminal including a set of three lumens. The set of three lumens includes, for example, a primary lumen 126 (e.g., a distal lumen), a secondary lumen 128 (e.g., a medial lumen), and a tertiary lumen 130 (e.g., a proximal lumen) formed of fluidly connected portions of three catheter-tube lumens, three hub lumens, and three extension-leg lumens. Whether the RICC 102 is monoluminal or multiluminal, the RICC 102 includes at least the primary lumen 126. The primary lumen 126 includes at least the one catheter-tube lumen set forth above that typically extends from the proximal end of the catheter tube 108 to the distal end of the catheter tube 108 as a catheter tube-lumen portion of the primary lumen 126, as well as a fluidly connected hub- and extension leg-lumen portions of the primary lumen 126. In accordance with the foregoing catheter-tube lumen, the introducing lumen 124 of the catheter tube 108 is coincident with a distal-end portion of the primary lumen 126, particularly the distal-end portion of the primary lumen 126 distal of the side aperture 116. In addition, the primary lumen 126 has a primary-lumen aperture 132 in the distal end of the RICC 102 (e.g., the distal end of the catheter tube 108 or the distal end of the catheter tip 114). The secondary lumen 128 has a secondary-lumen aperture 134 in the side of the catheter tube 108 proximal of the primary-lumen aperture 132 and distal of the following tertiary-lumen aperture 136 such that the secondary lumen 128 is between the primary-lumen aperture 132 and the tertiary-lumen aperture 136. The tertiary lumen 130 has a tertiary-lumen aperture 136 in the side of the catheter tube 108 proximal of the secondary-lumen aperture 134. The side aperture 116 of the catheter tube 108 can be between the primary-lumen aperture 132 and the secondary-lumen aperture 134, between the secondary-lumen aperture 134 and the tertiary-lumen aperture 136, or proximal of the tertiary-lumen aperture 136 as shown in FIG. 5 such that each lumen aperture of the primary-lumen aperture 132, the secondary-lumen aperture 134, and the tertiary-lumen aperture 136 is distal of the side aperture 116.

The RICC 102 can further include a maneuver guidewire 138. The maneuver guidewire 138 can include an atraumatic tip (e.g., a coiled or partially coiled tip) (not shown) and a length sufficient for advancing the maneuver guidewire 138 to the lower ⅓ of the superior vena cava ("SVC") of the heart. The maneuver guidewire 138 can be captively disposed in the RICC 102 in at least a ready-to-deploy state of the RICC assembly 100. For example, the maneuver guidewire 138 can be disposed in the primary lumen 126 of the RICC 102 with a proximal-end portion or a medial portion of the maneuver guidewire 138 disposed in the extension leg-lumen portion of the primary lumen 126, the medial portion or a distal-end portion of the maneuver guidewire 138 disposed in the hub-lumen portion of the primary lumen 126, and the distal-end portion of the maneuver guidewire 138 disposed in the catheter tube-lumen portion of the primary lumen 126, which is formed of the one catheter-tube lumen set forth above that typically extends from the proximal end of the catheter tube 108 to the distal end of the catheter tube 108. However, the distal-end portion of the foregoing catheter-tube lumen distal of the side aperture 116 is coincident with the introducing lumen 124, which, as set forth below, is occupied by the introducer needle 146 in at least the ready-to-deploy state of the RICC assembly 100. Due to the presence of the introducer needle 146 in the introducing lumen 124, a distal end of the maneuver guidewire 138 is just short of the side aperture 116 in at least the ready-to-deploy state of the RICC assembly 100.

The maneuver guidewire 138 includes a stop 140 (e.g., a hub, a ball, a slug, etc.) about a proximal-end portion of the maneuver guidewire 138 forming a stop end (e.g., a hub end, a ball end, a slug end, etc.) of the maneuver guidewire 138.

The stop end of the maneuver guidewire 138 is larger than a proximal-end opening of the primary lumen 126 or the extension leg-lumen portion thereof, thereby providing a distal limit for advancing the maneuver guidewire 138 into the RICC 102. In addition, the maneuver guidewire 138 can be disposed in a fixed-length sterile barrier 142 (e.g., a longitudinal bag) including a closed or sealed proximal end and an otherwise open distal end removably coupled (e.g., removably adhered) to a proximal end of the Luer connector of the extension leg for manual removal of both the sterile barrier 142 and the maneuver guidewire 138 when needed. A combination of the fixed length of the sterile barrier 142, the closed or sealed proximal end of the sterile barrier 142, and the distal end of the sterile barrier 142 coupled to the Luer connector provides a limited tract within which the maneuver guidewire 138 can proximally move, thereby providing a proximal limit for withdrawing the maneuver guidewire 138 from the RICC 102. The proximal limit keeps the atraumatic tip of the maneuver guidewire 138 in the primary lumen 126 where, in at least the embodiment of the atraumatic tip having the coiled or partially coiled tip, the atraumatic tip remains in a straightened or uncoiled state. This is advantageous for it can be particularly difficult to reinsert such a guidewire in a lumen of a medical device such as a catheter. Optionally, the stop end of the maneuver guidewire 138 is coupled (e.g., adhered) to the proximal end of the sterile barrier 142 to maintain the stop end of the maneuver guidewire 138 in the proximal end of the sterile barrier 142, thereby reducing a mismatch between a length of the proximal-end portion of the maneuver guidewire 138 extending beyond the proximal end of the RICC 102 (e.g., a proximal end of the Luer connector) and an unpleated length of the sterile barrier 142. Reducing the mismatch between the foregoing lengths reduces a likelihood of losing the stop end of the maneuver guidewire 138 in a medial portion of the sterile barrier 142, which could require time and effort to rematch that would be better spent focusing on the patient.

In addition to providing the proximal limit for withdrawing the maneuver guidewire 138 from the RICC 102, the sterile barrier 142 is configured to maintain sterility of the maneuver guidewire 138 both before use (e.g., shipping and handling, storage, etc.) of the RICC assembly 100 and during use of the RICC assembly 100. During use of the RICC assembly 100, the sterile barrier 142 is configured to provide a no-touch advancing means for advancing the maneuver guidewire 138 into a blood-vessel lumen of a patient upon establishing a needle tract thereto. Likewise, the sterile barrier 142 is configured to provide a no-touch withdrawing means for withdrawing the maneuver guidewire 138 from the blood-vessel lumen of the patient, for example, after the catheter tube 108 has been advanced over the maneuver guidewire 138.

The RICC 102 can further include stiffening stylets such as a stiffening stylet 144 in either lumen or both lumens of the secondary lumen 128 and the tertiary lumen 130 of the triluminal embodiment of the RICC 102 for stiffening the RICC 102. FIG. 1 illustrates one such stiffening stylet 144. Such stiffening stylets provide additional column strength to prevent buckling of the catheter tube 108 when the catheter tube 108 is inserted into an insertion site and advanced through a vasculature of a patient.

The introducer 104 includes an introducer needle 146, a syringe 148 operably connected to the introducer needle 146, and an access guidewire 150 disposed in the introducer 104. The introducer 104 can further include a fluid-pressure indicator 152 operably connected to the introducer needle 146. As set forth below, the introducer 104 is configured with at least two different actuation mechanisms (e.g., an actuation mechanism for withdrawing the plunger 166 and an actuation mechanism for advancing or withdrawing the access guidewire 150) actuated by using a single finger of a hand while holding a distal-end portion of the introducer 104 between a thumb and another finger or fingers of the same hand.

The introducer needle 146 includes a needle hub 154 and a needle shaft 156 extending from the needle hub 154, which needle shaft 156 terminates with a needle tip 158 (e.g., a beveled tip) in a distal-end portion of the needle shaft 156. The needle hub 154 includes a rib 155 configured to insert into the slot 189 of the distal coupler 186 and prevent the syringe 148 from rolling from side to side in at least the ready-to-deploy state of the RICC assembly 100. In addition, the needle hub 154 is translucent and preferably colorless for observing blood flashback from a venipuncture with the needle tip 158 (e.g., a beveled tip). When the RICC assembly 100 is in at least the ready-to-deploy state as shown in FIG. 1, little more than the needle tip 158 extends from the distal end of the RICC 102 for the venipuncture. Indeed, the distal-end portion (e.g., about 7 cm) of the needle shaft 156 extends through the longitudinal through hole of the distal coupler 186 of the coupling system 106 set forth below, through the side aperture 116 of the catheter tube 108, along the introducing lumen 124 of the catheter tube 108, and through the distal end of the RICC 102 when the RICC assembly 100 is in at least the ready-to-deploy state. However, in some embodiments, 2-3 cm or more of the distal-end portion of the needle shaft 156 can extend from the distal end of the RICC 102 for the venipuncture. In such embodiments, the first section 118 of the catheter tube 108 is shorter in length as opposed to the needle shaft 156 being longer in length.

When present, the fluid-pressure indicator 152 extends from a side arm 160 of the needle hub 154. The fluid-pressure indicator 152 includes a closed end and an open end fluidly coupled to a needle lumen of the introducer needle 146 by way of a side-arm lumen of the side arm 160. The fluid-pressure indicator 152 is configured as a built-in accidental arterial indicator, wherein blood under sufficient pressure (e.g., arterial blood) can enter the fluid-pressure indicator 152 and compress a column of air within the fluid-pressure indicator 152. However, it is also possible to observe the blood flashback from the venipuncture in the fluid-pressure indicator 152. That said, the blood flashback from the venipuncture is normally observed in the needle hub 154, the side arm 160 of the needle hub 154, or the syringe 148.

The syringe 148 includes a syringe housing 162 around a barrel 164, a plunger 166 disposed in the barrel 164, and a syringe tip 168 in a distal-end portion of the barrel 164, which is coupled to the needle hub 154 of the introducer needle 146 when the RICC assembly 100 is in at least the ready-to-deploy state. The syringe 148 also includes a syringe portion of the access-guidewire lumen 174.

The syringe housing 162 extends from a proximal-end portion to a distal end in a distal-end portion of the syringe housing 162 that can be coextensive with the distal-end portion of the barrel 164 as shown. The syringe housing 162 can include a gripping portion 170 (e.g., a pattern of bumps, through holes, etc.) in the distal-end portion thereof configured to facilitate gripping the syringe housing 162 and, thus, the introducer 104 by the distal-end portion thereof between the thumb and the other finger or fingers of the same hand set forth above. Distal placement of the gripping portion 170 about the distal-end portion of the syringe housing 162 encourages holding and handling the RICC assembly 100 in a location that provides better control of a distal-end portion of the RICC assembly 100 in that small inadvertent yaw- or pitch-type movements remain relatively small in the distal-end portion of the RICC assembly 100 compared to the same type of movements when the RICC assembly 100 is held in a more proximal location.

The syringe housing 162 and the plunger 166 are configured to operate together as a single unit insofar as actuating the syringe 148 (e.g., withdrawing the plunger 166 for aspirating blood). The syringe housing 162 and the plunger 166 or the end piece 180 thereof can be molded together in an integral piece such that the proximal-end portion of the syringe housing 162 is integral with a proximal-end portion of the plunger 166. Alternatively, the syringe housing 162 and the plunger 166 or the end piece 180 thereof can be separately molded and subsequently coupled together in a coupled piece such that the proximal-end portion of the syringe housing 162 is coupled to the proximal-end portion of the plunger 166 or the end piece 180 thereof. For example, an inner wall in a proximal end of the syringe housing 162 can be bonded or welded to a plunger flange of a distal end of the plunger 166 or the end piece 180 thereof. Whether the syringe housing 162 and the plunger 166 are integral with or coupled to each other, proximally sliding the syringe housing 162 relative to the barrel 164 withdraws the plunger 166 from the barrel 164, thereby actuating the syringe 148 as a single unit.

The syringe 148 can further include a push tab 172 proximally extending over the barrel 164 from the distal-end portion of the barrel 164 (e.g., from an integrated connector of the barrel 164 around the syringe tip 168) to which the push tab 172 is coupled. The push tab 172 is configured for use when actuating the syringe 148 as set forth above. Indeed, the push tab 172 is configured for pushing against with the single finger while holding the distal-end portion of the syringe housing 162 between the thumb and the other finger or fingers of the same hand set forth above, which proximally slides the syringe housing 162 relative to the barrel 164 and withdraws the plunger 166 from the barrel 164.

The syringe 148 also includes a syringe portion of an access-guidewire lumen 174 formed of fluidly connected portions of a plunger lumen of the plunger 166, a syringe-tip lumen of the syringe tip 168, and any space within the barrel 164 formed by pulling the plunger 166 partially out of the barrel 164 such as in an operating state of a number of operating states of the RICC assembly 100 (e.g., during the blood-aspirating step of the method set forth below). Another portion of the access-guidewire lumen 174 is the introducer-needle portion of the access-guidewire lumen 174, namely the needle lumen of the introducer needle 146, particularly when the introducer needle 146 is operably connected to the syringe 148 as in most states of the RICC assembly 100.

The plunger 166 includes a sealing mechanism 176 in a distal-end portion of the plunger 166 for sealing off the access-guidewire lumen 174 distal of the sealing mechanism 176. The sealing mechanism 176 is configured to seal off the access-guidewire lumen 174 to maintain a vacuum for aspirating blood when the plunger 166 is withdrawn from the barrel 164. The sealing mechanism 176 is also configured to seal off the access-guidewire lumen 174 to prevent blood from discharging (e.g., flashing back) through the longitudinal slots of the barrel 164 and the plunger 166 set forth below during a venipuncture or while withdrawing the access guidewire 150 from a blood-vessel lumen of a patient, thereby minimizing or preventing a potential for contaminating an operating field or any clinicians operating within the operating field.

As shown in FIG. 4, the sealing mechanism 176 can be a cartridge disposed in a cavity in a distal-end portion of a main body 178 of the plunger 166 and held in the cavity by an end piece 180 of the plunger 166. The cartridge is coaxially aligned with the access-guidewire lumen 174 or the plunger-lumen portion thereof such that an unwrapped, bare-wire portion the access guidewire 150 passes through proximal- and distal-end through holes of the cartridge, which have inner diameters commensurate with an outer diameter of the access guidewire 150. Optionally, the sealing mechanism 176 includes one or more gaskets such as 'O'-rings within the cartridge or as an alternative to the cartridge. Instead of the cartridge, for example, the one-or-more 'O'-rings can be axially compressed in the cavity by the end piece 180 of the plunger 166, which, in turn, radially compresses the 'O'-rings around the access guidewire 150, thereby sealing off the access-guidewire lumen 174.

The access guidewire 150 is captively disposed in the introducer 104 such that at least a portion of the access guidewire 150 is always in a portion (e.g., the plunger-lumen portion, the needle-lumen portion, etc.) of the access-guidewire lumen 174 no matter the state of the RICC assembly 100. For example, when the access guidewire 150 is withdrawn to its proximal limit (e.g., defined by the proximal ends of the longitudinal slots set forth below), a distal-end portion of the access guidewire 150 is disposed in at least a distal-end portion of the plunger lumen. Meanwhile, a proximal-end portion of the access guidewire 150 is disposed in a proximal-end portion of the plunger lumen. When the RICC assembly 100 is in at least the ready-to-deploy state thereof with a distal end of the access guidewire 150 just short of the needle tip 158, a medial portion of the access guidewire 150 is disposed between the distal-end portion of the plunger lumen and a proximal-end portion of the needle lumen. And when the access guidewire 150 is advanced to its distal limit (e.g., defined by the distal ends of the longitudinal slots set forth below) in some operating states of the number of operating states of the RICC assembly 100 (e.g., during the access guidewire-advancing step of the method set forth below), the proximal-end portion of the access guidewire 150 is disposed in at least the distal-end portion of the plunger lumen. Meanwhile, as result of its length, the distal-end portion of the access guidewire 150 extends through or beyond the distal end of the RICC 102, which is sufficient for extension of the access guidewire 150 into a blood vessel lumen of a patient upon establishing access thereto after the needle tract-establishing step set forth below.

The syringe 148 also includes a slider 182 (e.g., a tabbed slider) distally extending over the barrel 164 from the syringe housing 162. The slider 182 is configured for actuating the access guidewire 150 with the single finger of the same hand set forth above (e.g., with a scroll wheel-type motion of the finger like that used on a computer mouse) while holding the distal-end portion of the syringe housing 162 between the thumb and the other finger or fingers of the same hand. The slider 182 includes an extension 184 extending through a longitudinal slot (not shown) in each of the barrel 164 and the plunger 166 into the access-guidewire lumen 174 proximal of the sealing mechanism 176 where the extension 184 is coupled to the access guidewire 150. Proximal and distal ends of the longitudinal slots provide stops for the extension 184 and, therefore, a limited tract within which the extension 184 can proximally move, thereby providing proximal and distal limits for respectively withdrawing or advancing the access guidewire 150 into or from the introducer 104.

The coupling system 106 includes a distal coupler 186 and a proximal coupler 188 configured to couple the RICC 102 and the introducer 104 together by corresponding proximal-end and distal-end portions thereof in at least the ready-to-deploy state of the RICC assembly 100 while allowing the introducer 104 to slide relative to the RICC 102 (or vice versa).

The distal coupler 186 includes a catheter-tube clip configured to both slidably and removably attach the distal coupler 186 to the catheter tube 108 proximal of the side aperture 116. The distal coupler 186 also includes a longitudinal through hole, a slot 189, and a push tab 190 in a distal-end portion of the distal coupler 186. The needle shaft 156 of the introducer needle 146 extends through the longitudinal through hole of the distal coupler 186, through the side aperture 116 of the catheter tube 108, along the introducing lumen 124 of the catheter tube 108, and through the distal end of the RICC 102 when the RICC assembly 100 is in at least the ready-to-deploy state thereof. While the distal coupler 186 is slidably attached to the catheter tube 108, extension of the needle shaft 156 through the distal coupler 186 and the catheter tube 108 in accordance with the foregoing wedges the distal coupler 186 between the needle shaft 156 and the catheter tube 108 such that the distal coupler 186 remains in its location on the catheter tube 108 proximal of the side aperture 116 in at least the ready-to-deploy state of the RICC assembly 100. Indeed, only when the needle shaft 156 is removed from the distal coupler 186 is the distal coupler 186 able to slide over the catheter tube 108. The slot 189 is configured to accept insertion of the rib 155 of needle hub 154 therein and prevent the syringe 148 from rolling from side to side in at least the ready-to-deploy state of the RICC assembly 100. The push tab 190 is configured to allow a clinician to single handedly advance the RICC 102 off the needle shaft 156 with a single finger of a hand (e.g., with a flick-type motion of the finger) while holding the distal-end portion introducer 104 between a thumb and another finger or fingers of the same hand, thereby providing a no-touch mechanism for advancing the RICC 102, specifically the distal-end portion of the catheter tube 108, over the needle shaft 156 and into a blood-vessel lumen of a patient.

The proximal coupler 188 is an extension of the syringe housing 162 around the syringe 148, the proximal coupler 188 being either integral with the syringe housing 162 (e.g., molded together with the syringe housing 162) or coupled to the syringe housing 162 (e.g., molded separately from the syringe housing 162 and bonded or welded thereto). The proximal coupler 188 includes a catheter-hub clip configured to both slidably and removably attach to the catheter hub 110 or the one-or-more extension legs 112. The catheter-hub clip is configured for suspending the RICC 102 by the catheter hub 110 in at least the ready-to-deploy state of the RICC assembly 100, thereby keeping the RICC 102 from drooping. The catheter-hub clip is also configured for suspending the RICC 102 by the one-or-more extension legs 112 in some operating states of the number of operating states of the RICC assembly 100 (e.g., during the introducer-removing step of the method set forth below), thereby further keeping the RICC 102 from drooping.

The RICC 102 can further include a sterile barrier 192 (e.g., a collapsible or pleatable bag, a casing, etc.) configured to maintain sterility of the catheter tube 108 between the catheter hub 110 and the distal coupler 186 prior to insertion of the catheter tube 108 into a blood-vessel lumen of a patient. (See FIG. 2.) In at least the ready-to-deploy state of the RICC assembly 100, the sterile barrier 192 is over the catheter tube 108 between the catheter hub 110 about the proximal-end portion of the catheter tube 108 and the distal coupler 186, to which distal coupler 186 the sterile barrier 192 is coupled. The sterile barrier 192 is configured to split apart when a sterile-barrier pull tab 194 of the sterile barrier 192 is removed from the catheter-hub clip in which it is tucked and pulled away from the catheter tube 108, thereby providing a no-touch mechanism for removing the sterile barrier 192 from the catheter tube 108. The sterile barrier 192 has sufficient tensile strength to pull the distal coupler 186 off the catheter tube 108 without breaking when the sterile barrier 192 splits down to the distal coupler 186 while being pulled away from the catheter tube 108.

As set forth above, FIG. 1 illustrates the RICC assembly 100 in at least the ready-to-deploy state. While some operating states of the number of operating states of the RICC assembly 100 are also set forth above, additional operating states of the RICC assembly 100 can be discerned from steps of the method for inserting the RICC 102 set forth below.

Methods

A method of the RICC assembly 100 includes a method for inserting the RICC 102 into a blood-vessel lumen of a patient. Such a method includes, in some embodiments, a RICC assembly-obtaining step, a needle tract-establishing step, a first RICC-advancing step, and a needle-withdrawing step.

The RICC assembly-obtaining step includes obtaining the RICC assembly 100. As set forth above, the RICC assembly 100 includes the RICC 102, the introducer 104 including the syringe 148 coupled to the introducer needle 146, and the coupling system 106 including the distal coupler 186 that couples the RICC 102 and the introducer 104 together by the distal-end portions thereof in at least the ready-to-deploy state of the RICC assembly 100.

The method can further include a needle tip-ensuring step of ensuring the needle tip 158 extends from the distal end of the RICC 102 before the needle tract-establishing step. As set forth above, the needle shaft 156 extends through the longitudinal through hole of the distal coupler 186, through the side aperture 116 in the distal-end portion of the catheter tube 108, along the introducing lumen 124 of the catheter tube 108, and out the distal end of the RICC 102.

The needle tract-establishing step includes establishing a needle tract from an area of skin to the blood-vessel lumen of the patient with the introducer needle 146 while holding the distal-end portion of the syringe housing 162 around the barrel 164 of the syringe 148 between a thumb and another finger or fingers of a hand. Meanwhile, at least a single finger of the same hand is kept readily available. As set forth above, the needle shaft 156 extends through the longitudinal through hole of the distal coupler 186, through the side aperture 116 in the distal-end portion of the catheter tube 108 of the RICC 102, along the introducing lumen 124 of the catheter tube 108, and out the distal end of the RICC 102 for establishing the needle tract.

The needle tract-establishing step can further include ensuring blood flashes back into the needle hub 154 of the introducer needle 146, the side arm 160 of the needle hub 154, or the fluid-pressure indicator 152 extending from the side arm 160 of the needle hub 154 upon establishing the needle tract.

The method can further include a blood-aspirating step. The blood-aspirating step includes aspirating blood with the syringe 148 to confirm the needle tip 158 is disposed in the blood-vessel lumen of the patient before the needle-withdrawing step. The blood-aspirating step includes pushing the push tab 172 extending over the barrel 164 from the distal-end portion thereof with the single finger of the hand while holding the distal-end portion of the syringe housing 162 between the thumb and the other finger or fingers of the same hand, which proximally slides the syringe housing 162 relative to the barrel 164 and withdraws the syringe housing-connected plunger 166 from the barrel 164.

The method can further include an access guidewire-advancing step. The access guidewire-advancing step includes advancing the access guidewire 150 disposed in the access-guidewire lumen 174 into the blood-vessel lumen beyond the needle tip 158 of the introducer needle 146, which can be effectuated by distally advancing the slider 182 coupled to the access guidewire 150 over the barrel 164 with the single finger of the hand while holding the distal-end portion of the syringe housing 162 between the thumb and the other finger or fingers of the same hand. As set forth above, the access guidewire 150 is disposed in the access-guidewire lumen 174 formed of at least the plunger lumen of the plunger 166 and the needle lumen of the introducer needle 146, which facilitates first-stick success by making the access guidewire 150 immediately available before the blood-lumen vessel can be lost due to small inadvertent movements. The access guidewire-advancing step should be performed before the first RICC-advancing step such that the distal-end portion of the catheter tube 108 can be advanced over the access guidewire 150 as well.

The first RICC-advancing step includes advancing the distal-end portion of the first section 118 of the catheter tube 108 into the blood-vessel lumen over the needle shaft 156, the access guidewire 150, or both. As set forth above, the catheter tube 108 includes the first section 118 formed of the first material having the first durometer and the second section 120 formed of the second material having the second durometer less than the first durometer. The first section 118 of the catheter tube 108 is configured with a column strength for advancing the catheter tube 108 into the blood-vessel lumen over the access guidewire 150 or the maneuver guidewire 138 after the maneuver guidewire-advancing step set forth below. For example, the first RICC-advancing step can include advancing the catheter tube 108 into the blood-vessel lumen by the push tab 190 of the distal coupler 186 with the single finger of the hand (e.g., with a flick-type motion of the finger) while holding the introducer 104 by the distal-end portion of the syringe housing 162 between the thumb and the other finger or fingers of the same hand. The distal coupler 186 includes the push tab 190 configured for advancing the catheter tube 108 into the blood-vessel lumen with the single finger.

The first RICC-advancing step further includes advancing the catheter hub 110 of the RICC 102 from the catheter-hub clip of the proximal coupler 188 of the coupling system 106 and, thereafter, the one-or-more extension legs 112 of the RICC 102 within the catheter-hub clip. The RICC 102 is configured to suspend from the coupling system 106 until at least withdrawing the needle shaft 156 from both the introducing lumen 124 and the longitudinal through hole of the distal coupler 186 such as after the introducer-removing step set forth below.

The method can further include an access guidewire-withdrawing step of withdrawing the access guidewire 150 from the blood-vessel lumen of the patient such as by proximally advancing the slider 182 coupled to the access guidewire 150 over the barrel 164 with the single finger of the hand while holding the distal-end portion of the syringe housing 162 between the thumb and the other finger or fingers of the same hand. The access guidewire-withdrawing step can be performed after the first RICC-advancing step such as after the distal-end portion of the catheter tube 108 is suitably placed within the blood-vessel lumen over both the needle shaft 156 and the access guidewire 150.

The needle-withdrawing step includes withdrawing the needle shaft 156 from the introducing lumen 124 by way of the side aperture 116 of the catheter tube 108. Like the access guidewire-withdrawing step, the needle-withdrawing step can be performed after the first RICC-advancing step such as after the distal-end portion of the catheter tube 108 is suitably placed within the blood-vessel lumen over both the needle shaft 156 and the access guidewire 150.

The method can further include an introducer-removing step of completely removing the introducer 104 from the RICC assembly 100 after the needle-withdrawing step. The introducer-removing step includes withdrawing the needle shaft 156 from the longitudinal through hole of the distal coupler 186 while proximally sliding the catheter-hub clip along the one-or-more extension legs 112. Upon withdrawing the needle shaft 156 from the longitudinal through hole of the distal coupler 186, each extension leg of the one-or-more extension legs 112 can be removed through an opening in the catheter-hub clip, which opening is commensurate with or slightly wider than the diameter of an extension leg.

The method can further include a maneuver guidewire-advancing step. The maneuver guidewire-advancing step includes advancing the maneuver guidewire 138 into the blood-vessel lumen by way of, for example, the primary lumen 126 having the primary-lumen aperture 132 in the distal end of the RICC 102. As set forth above, the introducing lumen 124 of the catheter tube 108 is coincident with the distal-end portion of the primary lumen 126, particularly the distal-end portion of the primary lumen 126 distal of the side aperture 116. Therefore, the needle-withdrawing step must be performed before the maneuver guidewire-advancing step to ensure the primary lumen 126, or the introducing lumen 124 thereof, is free of both the needle shaft 156 and the access guidewire 150.

The method can further include a second RICC-advancing step. The second RICC-advancing step includes advancing the distal-end portion of the first section 118 of catheter tube 108 farther into the blood-vessel lumen (e.g., to the SVC) over the maneuver guidewire 138. The maneuver guidewire 138 provides the second section 120 of the catheter tube 108 columnar strength for the second RICC-advancing step. Concomitantly, the second catheter-advancing step includes sliding the distal coupler 186 proximally towards the proximal-end portion of the catheter tube 108 (e.g., toward the catheter hub 110) to uncover the catheter tube 108. As set forth above, the catheter tube 108 can be covered by the collapsible sterile barrier 192 between the proximal-end portion of the catheter tube 108 and the distal coupler 186 in at least the ready-to-deploy state of the RICC assembly 100.

The method can further include a sterile barrier-removing step. The sterile barrier-removing step includes removing the sterile barrier 192 and the distal coupler 186 from the RICC 102 by pulling the sterile-barrier pull tab 194 of the sterile barrier 192 opposite the distal coupler 186 away from the catheter tube 108 to split the sterile barrier 192 apart, then pulling the distal coupler 186 from the catheter tube 108 by the sterile barrier 192 to which the distal coupler 186 is slidably attached. Alternatively, the sterile barrier-removing step includes removing the distal coupler 186 and the sterile barrier 192 from the RICC 102 by pulling the distal coupler 186 away from the catheter tube 108 to split the sterile barrier 192 apart, then pulling the distal coupler 186 further proximally toward the proximal-end portion of the catheter tube 108 to completely remove the sterile barrier 192.

The method can further include a maneuver guidewire-withdrawing step of withdrawing the maneuver guidewire 138 from the blood-vessel lumen of the patient, as well as withdrawing the maneuver guidewire 138 from the RICC 102.

While some particular embodiments have been disclosed herein, and while the particular embodiments have been disclosed in some detail, it is not the intention for the particular embodiments to limit the scope of the concepts provided herein. Additional adaptations and/or modifications can appear to those of ordinary skill in the art, and, in broader aspects, these adaptations and/or modifications are encompassed as well. Accordingly, departures may be made from the particular embodiments disclosed herein without departing from the scope of the concepts provided herein.

What is claimed is:

1. A rapidly insertable central catheter ("RICC") assembly for direct insertion into a blood-vessel lumen of a patient, comprising:
    a RICC including:
        a catheter tube including a side aperture through a side of the catheter tube in a distal-end portion thereof, the side aperture opening into an introducing lumen of the catheter tube that extends from at least the side aperture to a distal end of the RICC;
        a catheter hub coupled to a proximal-end portion of the catheter tube; and
        one or more extension legs, each extension leg of the one-or-more extension legs coupled to the catheter hub by a distal-end portion thereof;
    an introducer configured to be actuated with a single finger of a hand while holding a distal-end portion of the introducer between a thumb and another finger or fingers of the hand, the introducer including:
        an introducer needle having a needle shaft extending through the distal end of the RICC when the RICC assembly is in at least a ready-to-deploy state of the RICC assembly; and
        a syringe including:
            a barrel having a syringe tip in a distal-end portion thereof coupled to a needle hub of the introducer needle in at least the ready-to-deploy state of the RICC assembly;
            a plunger disposed in the barrel; and
            a syringe housing encircling the barrel having a distal-end portion and a proximal-end portion, the proximal-end portion of the syringe housing either integral with or coupled to a proximal-end portion of the plunger such that proximally sliding the syringe housing relative to the barrel withdraws the plunger from the barrel; and
    a coupling system configured to couple the RICC and the introducer together, the coupling system including a distal coupler slidably attached to the catheter tube proximal of the side aperture.

2. The RICC assembly of claim 1, the catheter tube further including:
    a first section formed of a first material having a first durometer, the side aperture proximal of the first section of the catheter tube; and
    a second section formed of a second material having a second durometer less than the first durometer, the catheter tube thereby configured with both column strength and compliance for advancing the catheter tube into the blood-vessel lumen and through a vasculature of the patient.

3. The RICC assembly of claim 1, wherein the needle shaft further extends through a longitudinal through hole of the distal coupler, through the side aperture of the catheter tube, and along the introducing lumen of the catheter tube before exiting through the distal end of the RICC when the RICC assembly is in at least the ready-to-deploy state thereof.

4. The RICC assembly of claim 1, wherein the distal coupler includes a push tab configured to allow a clinician to single handedly advance the RICC off the needle shaft with the single finger of the hand while holding the distal-end portion of the introducer between the thumb and the other finger or fingers of the hand.

5. The RICC assembly of claim 1, the syringe further including a push tab proximally extending over the barrel from the distal-end portion of the barrel to which the push tab is coupled, the push tab configured for pushing against with the single finger while holding the distal-end portion of the syringe housing between the thumb and the other finger or fingers of the hand to proximally slide the syringe housing relative to the barrel and withdraw the plunger from the barrel.

6. The RICC assembly of claim 1, the introducer further including an access guidewire disposed in an access-guidewire lumen formed of at least a plunger lumen of the plunger and a needle lumen of the introducer needle, the access guidewire having a length sufficient for extension of the access guidewire through the distal end of the RICC and into the blood-vessel lumen of the patient.

7. The RICC assembly of claim 6, wherein the plunger includes a sealing mechanism in a distal-end portion of the plunger for sealing off the access-guidewire lumen distal of the sealing mechanism, the sealing mechanism configured to maintain a vacuum for aspirating blood when the plunger is withdrawn from the barrel.

8. The RICC assembly of claim 6, the syringe further including a slider distally extending over the barrel from the syringe housing configured for actuating the access guidewire with the single finger while holding the distal-end portion of the syringe housing between the thumb and the other finger or fingers of the hand, the slider including an extension extending through a longitudinal slot in each of the barrel and the plunger into the access-guidewire lumen proximal of the sealing mechanism where the extension is coupled to the access guidewire.

9. The RICC assembly of claim 1, the introducer further including a fluid-pressure indicator extending from a side arm of the needle hub, the fluid-pressure indicator fluidly coupled to the needle lumen of the introducer needle by way of a side-arm lumen of the side arm for observing blood flashback due to an accidental arterial puncture.

10. The RICC assembly of claim 1, the coupling system further including a proximal coupler coupled to the syringe and slidably attached to the catheter hub in at least the ready-to-deploy state of the RICC assembly, the coupling system configured to allow the RICC to slide relative to the introducer.

11. The RICC assembly of claim 10, wherein the proximal coupler includes a catheter-hub clip from which the RICC is configured to suspend by the catheter hub in at least the ready-to-deploy state of the RICC assembly or the one-ormore extension legs when the proximal coupler is advanced thereover in an operating state of the RICC assembly.

12. The RICC assembly of claim 11, the RICC further including a collapsible catheter-tube sterile barrier over the catheter tube between the catheter hub and the distal coupler to which distal coupler the catheter-tube sterile barrier is coupled, the catheter-tube sterile barrier configured to split apart when a sterile-barrier pull tab of the catheter-tube sterile barrier is removed from the catheter-hub clip and the catheter-tube sterile barrier is pulled away from the catheter tube by the sterile-barrier pull tab.

13. The RICC assembly of claim 12, wherein the catheter-tube sterile barrier has sufficient tensile strength to pull the distal coupler off the catheter tube without breaking when the catheter-tube sterile barrier splits down to the distal coupler while being pulled away from the catheter tube.

14. The RICC assembly of claim 1, wherein the RICC includes a set of three lumens including a primary lumen, a secondary lumen, and a tertiary lumen formed of fluidly connected portions of three catheter-tube lumens, three hub lumens, and three extension-leg lumens, the introducing lumen of the catheter tube coincident with a distal-end portion of the primary lumen.

15. The RICC assembly of claim 14, wherein the primary lumen has a primary-lumen aperture in a distal end of the RICC, the secondary lumen has a secondary-lumen aperture in the side of the catheter tube distal of the side aperture, and the tertiary lumen has a tertiary-lumen aperture in the side of the catheter tube distal of the side aperture but proximal of the secondary-lumen aperture.

16. The RICC assembly of claim 1, the RICC further including a maneuver guidewire disposed in the primary lumen having a length sufficient for extension of the maneuver guidewire to a lower ⅓ of a superior vena cava of a heart, the maneuver guidewire captively disposed in the RICC by a stop about a proximal-end portion of the maneuver guidewire and a closed end of a fixed-length maneuver-guidewire sterile barrier coupled to a Luer connector, the stop providing a distal limit to advancing the maneuver guidewire and the closed end of the maneuver-guidewire sterile barrier around the maneuver guidewire providing a proximal limit to withdrawing the maneuver guidewire.

17. A rapidly insertable central catheter ("RICC") assembly for direct insertion into a blood-vessel lumen of a patient, comprising:
a RICC including a catheter tube including a side aperture through a side of the catheter tube in a distal-end portion thereof, the side aperture opening into an introducing lumen of the catheter tube that extends from at least the side aperture to a distal end of the RICC;
an introducer including:
an introducer needle having a needle shaft extending through the distal end of the RICC; and
a syringe including:
a barrel having a syringe tip in a distal-end portion thereof coupled to a needle hub of the introducer needle; and
a syringe housing encircling a barrel of the syringe, the syringe housing having a distal-end portion and a proximal-end portion, the proximal-end portion of the syringe housing either integral with or coupled to a proximal-end portion of the plunger such that proximally sliding the syringe housing relative to the barrel withdraws the plunger from the barrel; and
a coupling system configured to couple the RICC and the introducer together, the coupling system including a distal coupler slidably attached to the catheter tube proximal of the side aperture.

18. The RICC assembly of claim 17, the syringe further including a push tab proximally extending over the barrel from the distal-end portion of the barrel to which the push tab is coupled, the push tab configured for pushing against with a single finger of a hand while holding the distal-end portion of the syringe housing between a thumb and another finger or fingers of the hand to proximally slide the syringe housing relative to the barrel and withdraw the plunger from the barrel.

19. The RICC assembly of claim 17, the introducer further including an access guidewire disposed in an access-guidewire lumen formed of at least a plunger lumen of the plunger and a needle lumen of the introducer needle, the access guidewire having a length sufficient for extension of the access guidewire through the distal end of the RICC and into the blood-vessel lumen of the patient.

20. The RICC assembly of claim 19, wherein the plunger includes a sealing mechanism in a distal-end portion of the plunger for sealing off the access-guidewire lumen distal of the sealing mechanism, the sealing mechanism configured to maintain a vacuum for aspirating blood when the plunger is withdrawn from the barrel.

21. The RICC assembly of claim 19, the syringe further including a slider distally extending over the barrel from the syringe housing configured for actuating the access guidewire with a single finger of a hand while holding the distal-end portion of the syringe housing between a thumb and another finger or fingers of the hand, the slider including an extension extending through a longitudinal slot in each of the barrel and the plunger into the access-guidewire lumen proximal of the sealing mechanism where the extension is coupled to the access guidewire.

* * * * *

UNITED STATES PATENT AND TRADEMARK OFFICE
CERTIFICATE OF CORRECTION

| | | |
|---|---|---|
| PATENT NO. | : 12,161,820 B2 | Page 1 of 1 |
| APPLICATION NO. | : 17/358504 | |
| DATED | : December 10, 2024 | |
| INVENTOR(S) | : Glade H. Howell et al. | |

It is certified that error appears in the above-identified patent and that said Letters Patent is hereby corrected as shown below:

In the Claims

Column 19, Line 36: Replace "one-or-more" with --one or more--.

Column 20, Line 42: Replace "6" with --7--.

Column 20, Line 52: Replace "1" with --6--.

Column 20, Line 67: Replace "one-or-" with --one or--.

Column 21, Line 31: Replace "1" with --14--.

Column 22, Line 7: Replace the second instance of "a" with --the--.

Column 22, Line 11: Replace "the" with --a--.

Column 22, Line 41: Replace "19" with --20--.

Signed and Sealed this
Sixth Day of May, 2025

Coke Morgan Stewart
*Acting Director of the United States Patent and Trademark Office*